(12) United States Patent
Inoue et al.

(10) Patent No.: US 8,329,903 B2
(45) Date of Patent: Dec. 11, 2012

(54) LIGHT-EMITTING ELEMENT INCLUDING ORGANOMETALLIC COMPLEX INCLUDING PYRAZINE DERIVATIVE

(75) Inventors: Hideko Inoue, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/353,829

(22) Filed: Jan. 19, 2012

(65) Prior Publication Data
US 2012/0123117 A1 May 17, 2012

Related U.S. Application Data

(62) Division of application No. 12/604,044, filed on Oct. 22, 2009, now Pat. No. 8,101,755.

(30) Foreign Application Priority Data

Oct. 23, 2008 (JP) ................................ 2008-273194

(51) Int. Cl.
C07D 241/00 (2006.01)
C01G 55/00 (2006.01)
(52) U.S. Cl. ........................................ 544/336; 423/22
(58) Field of Classification Search ............... 423/22; 544/336
See application file for complete search history.

(56) References Cited

U.S. PATENT DOCUMENTS

| | | |
|---|---|---|
| 2005/0221123 A1 | 10/2005 | Inoue et al. |
| 2005/0253135 A1 | 11/2005 | Stossel et al. |
| 2006/0127696 A1 | 6/2006 | Stossel et al. |
| 2007/0244320 A1 | 10/2007 | Inoue et al. |
| 2009/0183982 A1 | 7/2009 | Inoue et al. |

FOREIGN PATENT DOCUMENTS

| | | |
|---|---|---|
| DE | 102 38 903 A1 | 3/2004 |
| JP | 2002-105055 | 4/2002 |
| WO | WO 2004/037836 A1 | 5/2004 |

OTHER PUBLICATIONS

Zhang, G-L et al, "Synthesis and Phosphorescence of a New Iridium(III) Pyrazine Complex," Wuli Huaxue Xuebao, Acta Physico-Chimica Sinica, vol. 19, No. 10, Oct. 19, 2003, pp. 889-891 (with English translation).
Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English translation).
O'Brien, D.F. et al, "Improved Energy Transfer in Electrophosphorescent Devices," Applied Physics Letters, vol. 74, No. 3, Jan. 18, 1999, pp. 442-444.
Inoue, H. et al, "A Reaction of Singlet Oxygen with an Unsaturated Organic Molecule, 6.1.4, Quencher and Photosensitizer," Basic Chemistry Course Photochemistry I, Maruzen Co., Ltd., Sep. 30, 1999, pp. 106-110 (with English abstract).
Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L1502-L1504.
Baldo, M.A. et al, "High-Efficiency Fluorescent Organic Light-Emitting Devices Using a Phosphorescent Sensitizer," Nature, vol. 403, Feb. 17, 2000, pp. 750-753.
Thompson, M.E. et al, "Phosphorescent Materials and Devices," Proceedings of the 10th International Workshop on Inorganic and Organic Electroluminescence, EL '00, Dec. 4, 2000, pp. 35-38.
Duan, J-P. et al, "New Iridium Complexes as Highly Efficient Orange-Red Emitters in Organic Light-Emitting Diodes," Advanced Materials, vol. 15, No. 3, Feb. 5, 2003, pp. 224-228.
Zhang, G-L et al, "Synthesis and Phosphorescence of a New Iridium(III) Pyrazine Complex," Wuli Huaxue Xuebao, Acta Physico-Chimica Sinica, vol. 19, No. 10, Oct. 19, 2003, pp. 889-891 (with English abstract).
Slater, J.W. et al, "Cyclometallated Nitrogen Heterocycles," Journal of Organo Metallic Chemistry, vol. 688, Aug. 29, 2003, pp. 112-120.

(Continued)

*Primary Examiner* — Douglas M Willis
(74) *Attorney, Agent, or Firm* — Husch Blackwell LLP

(57) ABSTRACT

An organometallic complex is provided by which favorable red-color light emission can be obtained. Further, an organometallic complex having a peak of light emission at about 620 nm is provided because the wavelength of light which is perceived as excellent red-color light is about 620 nm. Furthermore, an organometallic complex is provided by which red-color light emission with high luminous efficiency (cd/A) can be obtained. An organometallic complex represented by the following general formula (G2) and a light-emitting element, a light-emitting device, and an electronic device including the organometallic complex represented by the following general formula (G2) are provided.

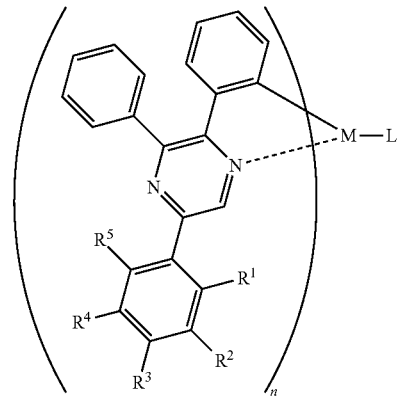

(G2)

7 Claims, 11 Drawing Sheets

OTHER PUBLICATIONS

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).

European Search Report re application No. EP 07005200.6, dated Jul. 23, 2007.

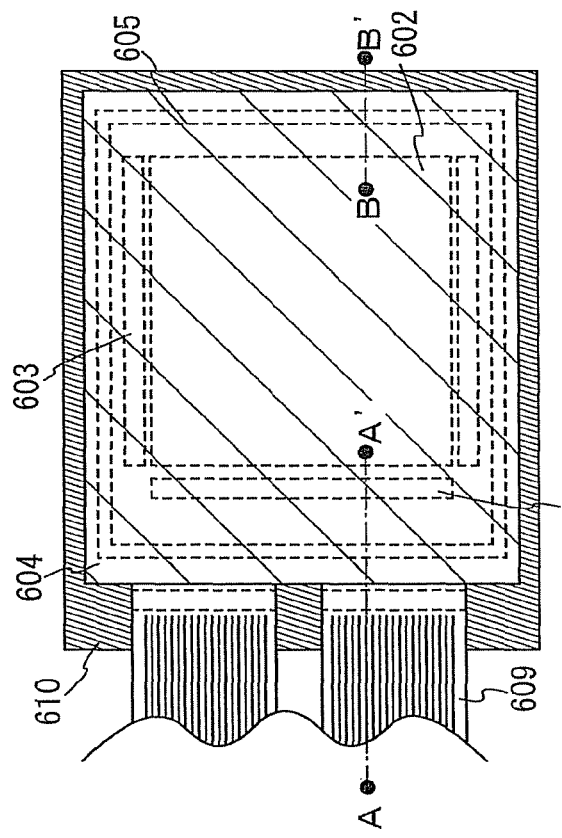
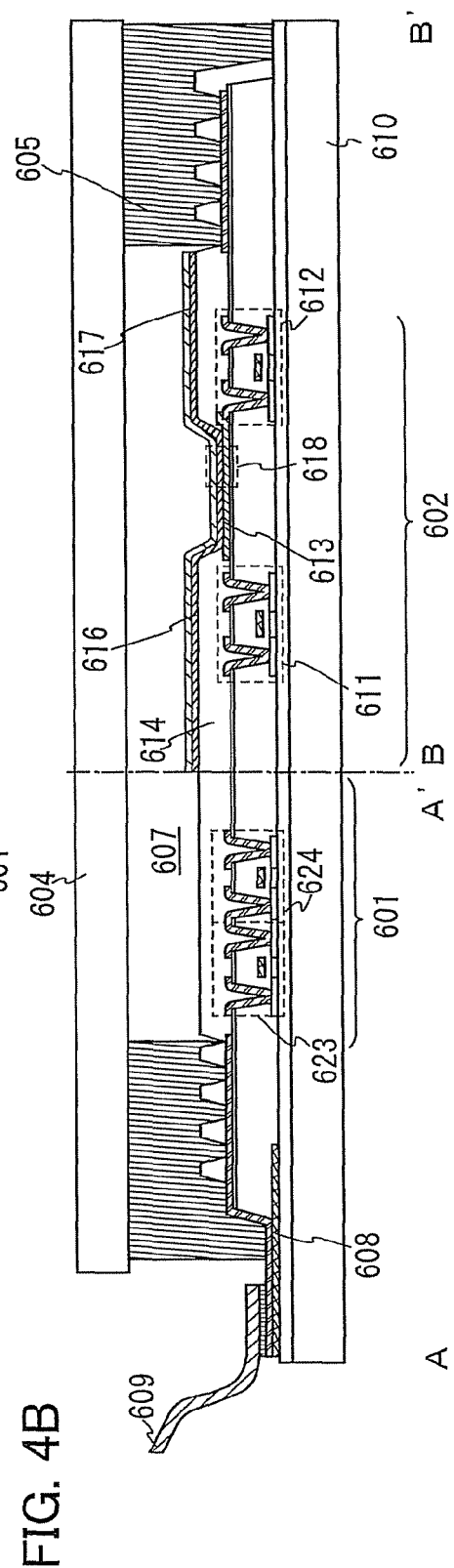
FIG. 4A
FIG. 4B

LIGHT-EMITTING ELEMENT INCLUDING ORGANOMETALLIC COMPLEX INCLUDING PYRAZINE DERIVATIVE

This application is a divisional of application Ser. No. 12/604,044 filed on Oct. 22, 2009 now U.S. Pat. No. 8,101,755.

BACKGROUND OF THE INVENTION

1. Field of the Invention

The present invention relates to an organometallic complex. In particular, the present invention relates to an organometallic complex that is capable of converting a triplet excited state into luminescence. Further, the present invention relates to a light-emitting element, a light-emitting device, and an electronic device which include the organometallic complex.

2. Description of the Related Art

Organic compounds are brought into an excited state by absorbing light. By going through this excited state, various reactions (photochemical reactions) are caused in some cases, or luminescence is produced in some cases. Therefore, various applications of the organic compounds have been being made.

As one example of the photochemical reactions, a reaction (oxygen addition) of singlet oxygen with an unsaturated organic molecule is known (for example, see Non-Patent Document 1). Since the ground state of an oxygen molecule is a triplet state, oxygen in a singlet state (singlet oxygen) is not generated by a direct photoexcitation. However, in the presence of another triplet excited molecule, singlet oxygen is generated to achieve an oxygen addition reaction. In this case, a compound that can become the triplet excited molecule is referred to as a photosensitizer.

As described above, in order to generate singlet oxygen, a photosensitizer that can become a triplet excited molecule by photoexcitation is necessary. However, since the ground state of an ordinary organic compound is a singlet state, photoexcitation to a triplet excited state is a forbidden transition, and a triplet excited molecule is unlikely to be generated. Therefore, as such a photosensitizer, a compound in which intersystem crossing from the singlet excited state to the triplet excited state easily occurs (or a compound in which the forbidden transition of photoexcitation directly to the triplet excited state is allowed) is required. In other words, such a compound can be used as a photosensitizer, and is useful.

Further, such a compound often emits phosphorescence. Phosphorescence refers to luminescence generated by transition between different energies in multiplicity. In an ordinary organic compound, phosphorescence refers to luminescence generated in returning from the triplet excited state to the singlet ground state (in contrast, luminescence in returning from a singlet excited state to a singlet ground state is referred to as fluorescence). Application fields of a compound capable of emitting phosphorescence, that is, a compound capable of converting an energy difference between a triplet excited state and a ground state into luminescence (hereinafter, referred to as a phosphorescent compound), include a light-emitting element using an organic compound as a light-emitting substance.

This light-emitting element has a simple structure in which a light-emitting layer including an organic compound that is a light-emitting substance is provided between electrodes. This light-emitting element has attracted attention as a next-generation flat panel display element in terms of characteristics such as being thin and light in weight, high-speed response, and direct current low voltage driving. In addition, a display device using this light-emitting element is superior in contrast, image quality, and wide viewing angle.

The light-emitting element including an organic compound as a light-emitting substance has a mechanism of light emission that is carrier injection: voltage is applied between electrodes where a light-emitting layer is interposed, electrons and holes injected from the electrodes are recombined to make the light-emitting substance excited, and then light is emitted in returning from the excited state to the ground state. As in the case of photoexcitation described above, types of the excited state include a singlet excited state (S*) and a triplet excited state (T*). The statistical generation ratio thereof in the light-emitting element is considered to be S*:T*=1:3.

As for a compound capable of converting a singlet excited state to luminescence (hereinafter, referred to as a fluorescent compound), luminescence from a triplet excited state (phosphorescence) is not observed but only luminescence from a singlet excited state (fluorescence) is observed at a room temperature. Accordingly, the internal quantum efficiency (the ratio of generated photons to injected carriers) in a light-emitting element using a fluorescent compound is assumed to have a theoretical limit of 25% based on S*:T*=1:3.

On the other hand, in the case of a light-emitting element including the phosphorescent compound described above, the internal quantum efficiency thereof can be improved to 75% to 100% in theory; namely, the emission efficiency thereof can be 3 to 4 times as much as that of a light-emitting element including a fluorescent compound. Therefore, the light-emitting element including a phosphorescent compound has been actively developed in recent years in order to achieve a high efficient light-emitting element (for example, see Non-Patent Document 2). An organometallic complex that contains iridium or the like as a central metal is particularly has attracted attention as a phosphorescent compound because of its high phosphorescence quantum efficiency.

REFERENCE

Non-Patent Document

[Non-Patent Document 1] Haruo INOUE, et al., Basic Chemistry Course PHOTOCHEMISTRY I (Maruzen Co., Ltd.), pp. 106-110

[Non-Patent Document 2] Zhang, Guo-Lin, et al., Gaodeng Xuexiao Huaxue Xuebao (2004), vol. 25, No. 3, pp. 397-400

The organometallic complex disclosed in Non-Patent Document 2 can be expected to serve as a photosensitizer, since it easily causes intersystem crossing. In addition, since the organometallic complex easily generates luminescence (phosphorescence) from a triplet excited state, a high efficient light-emitting element is expected by using the organometallic complex for the light-emitting element. However, in the present state, the number of types of such organometallic complexes is small.

Further, the organometallic complex disclosed in Non-Patent Document 2 emits orange-color light. In the case of using the organometallic complex for a full-color display, color purity of a red color is poor, which is a disadvantage in terms of color reproducibility. In contrast, in the case where the light-emitting color is in a dark red region; in other words, where the emission wavelength is extremely long, the organometallic complex is advantageous in terms of color reproducibility; however, the luminous efficiency (cd/A) is decreased.

In consideration of the above-described problems, it is an object of one embodiment of the present invention to provide an organometallic complex by which favorable red-color light emission can be obtained. It is another object to provide an organometallic complex having a peak of light emission at about 620 nm because the wavelength of light which is perceived as excellent red-color light by human eyes is about 620 nm. It is another object to provide an organometallic complex by which red-color light emission with high luminous efficiency can be obtained.

It is another object to provide a light-emitting element with high emission efficiency. Further, it is another object to provide a light-emitting element by which red-color light emission with high luminous efficiency can be obtained. Furthermore, it is another object to provide a light-emitting device and an electronic device with low power consumption.

SUMMARY OF THE INVENTION

The present inventors have made researches keenly. As a result, the present inventors have invented that a pyrazine derivative represented by the following general formula (G0) is ortho metalated with a metal ion of Group 9 or Group 10 in the periodic table, thereby an organometallic complex can be formed. Further, the present inventors have found that the organometallic complex easily causes intersystem crossing and can emit phosphorescence efficiently. Furthermore, they have also found that the light-emitting color of the organometallic complex, which has a peak of emission wavelength at about 620 nm, is favorable red color.

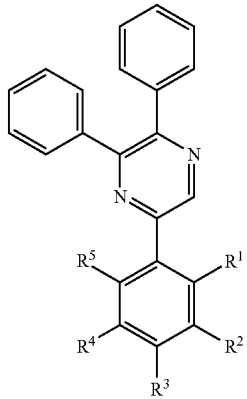

(G0)

In the formula, $R^1$ to $R^5$ each represent hydrogen or a cyano group, and at least one of $R^1$ to $R^5$ is a cyano group.

Note that a cyano group is preferably applied to any one of $R^1$ to $R^5$ in terms of easiness of synthesizing an organometallic complex.

Further, since a structure in which the pyrazine derivative represented by the above-mentioned general formula (G0) is ortho-metalated contributes to emission of phosphorescence greatly, the organometallic complex having a partial structure represented by the following general formula (G1) is given as one embodiment of the present invention.

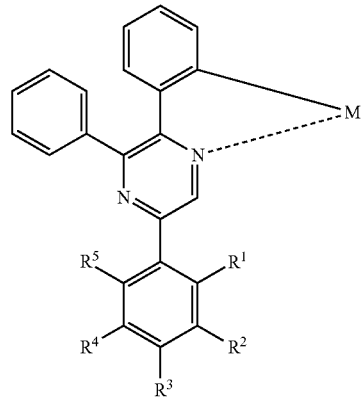

(G1)

In the formula, $R^1$ to $R^5$ each represent hydrogen or a cyano group, and at least one of $R^1$ to $R^5$ is a cyano group. Further, M represents a central metal which is an element belonging to Group 9 or Group 10.

Note that a cyano group is preferably applied to any one of $R^1$ to $R^5$ in terms of easiness of synthesizing an organometallic complex.

Here, as the organometallic complex having the structure represented by the general formula (G1), specifically, an organometallic complex represented by the following general formula (G2) is preferable since it is easy to synthesize.

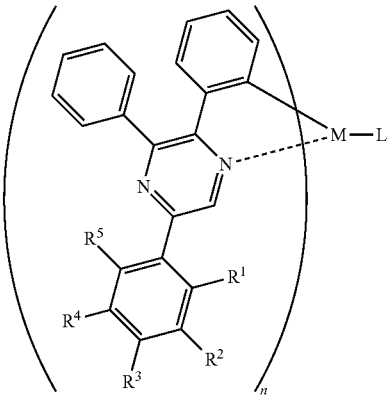

(G2)

In the formula, $R^1$ to $R^5$ each represent hydrogen or a cyano group, and at least one of $R^1$ to $R^5$ is a cyano group. Further, M represents a central metal which is an element belonging to Group 9 or Group 10. Furthermore, n is 2 when the central metal is an element belonging to Group 9, and n is 1 when the central metal is an element belonging to Group 10. Furthermore, L represents a monoanionic ligand.

Note that a cyano group is preferably applied to any one of $R^1$ to $R^5$ in terms of easiness of synthesizing an organometallic complex. Therefore, an organometallic complex of one embodiment of the present invention is represented by the following general formula (G3), (G4), or (G5).

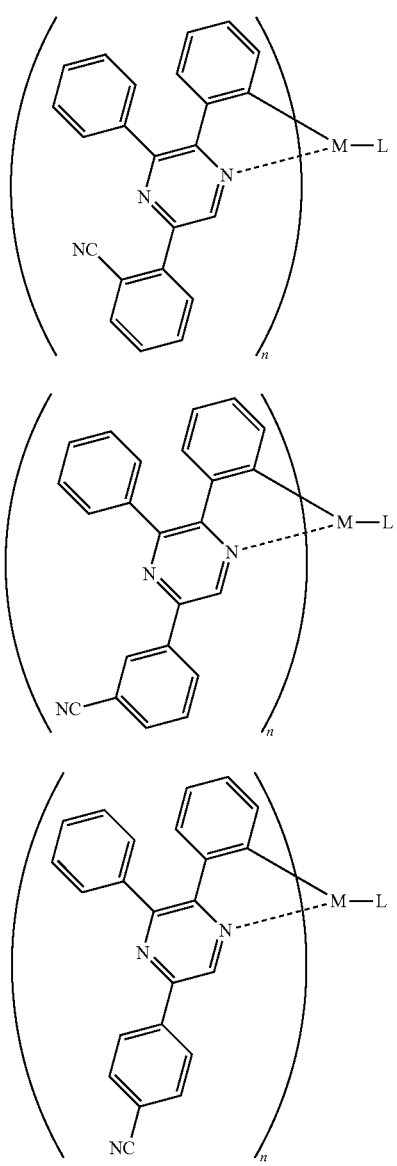

(G3)

(G4)

(G5)

In the general formulae (G3), (G4), and (G5), M represents a central metal which is an element belonging to Group 9 or Group 10. Further, n is 2 when the central metal is an element belonging to Group 9, and n is 1 when the central metal is an element belonging to Group 10. Furthermore, L represents a monoanionic ligand.

Note that the above-mentioned monoanionic ligand L is preferably any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen, because these ligands have high coordinating ability. More preferably, the monoanionic ligand L is a monoanionic ligand represented by any of the following structural formulae (L1) to (L8). Since these ligands have high coordinating ability and can be obtained at low price, they are useful.

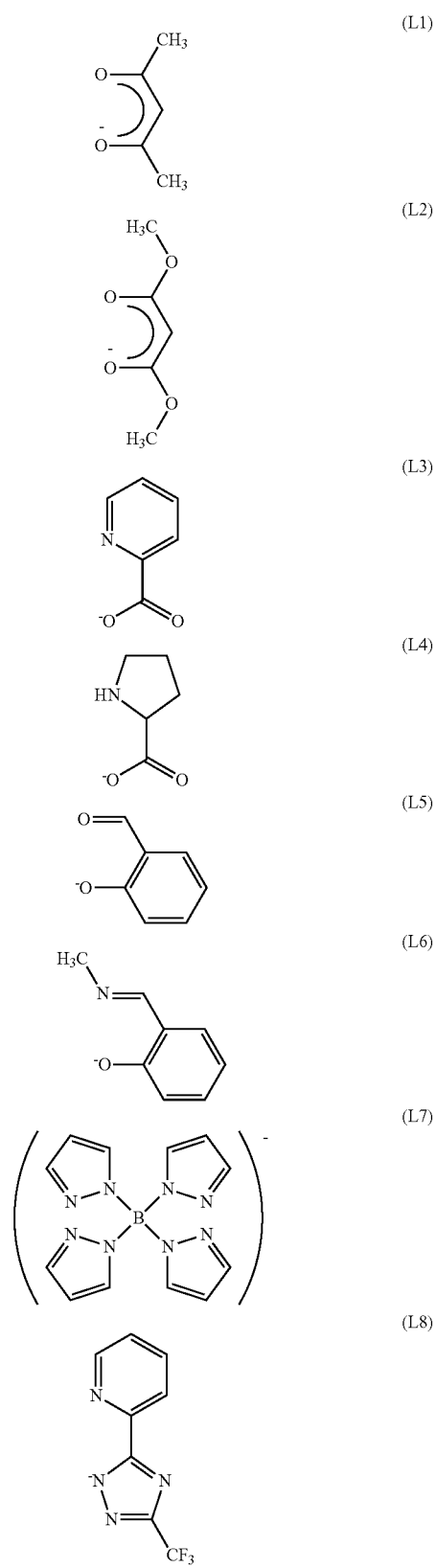

(L1)

(L2)

(L3)

(L4)

(L5)

(L6)

(L7)

(L8)

In order to obtain emission of phosphorescence more efficiently from an organometallic complex of one embodiment of the present invention represented by each of the general formulae (G1) to (G5), a heavy metal is preferable as the central metal in terms of heavy atom effect. Therefore, as for the above organometallic complex, the central metal M is preferably iridium or platinum. Particularly when the central metal M is iridium, heat resistance of the organometallic complex is improved. Therefore, iridium is particularly preferable as the central metal M. Further, in terms of light-emitting color, the ligand represented by the structural formula (L1) is preferable as a ligand L among the above-mentioned ligands represented by any of the structural formulae (L1) to (L8). Therefore, an organometallic complex represented by the following structural formula (1), (2), or (3) is preferable as the structure represented by the general formula (G2).

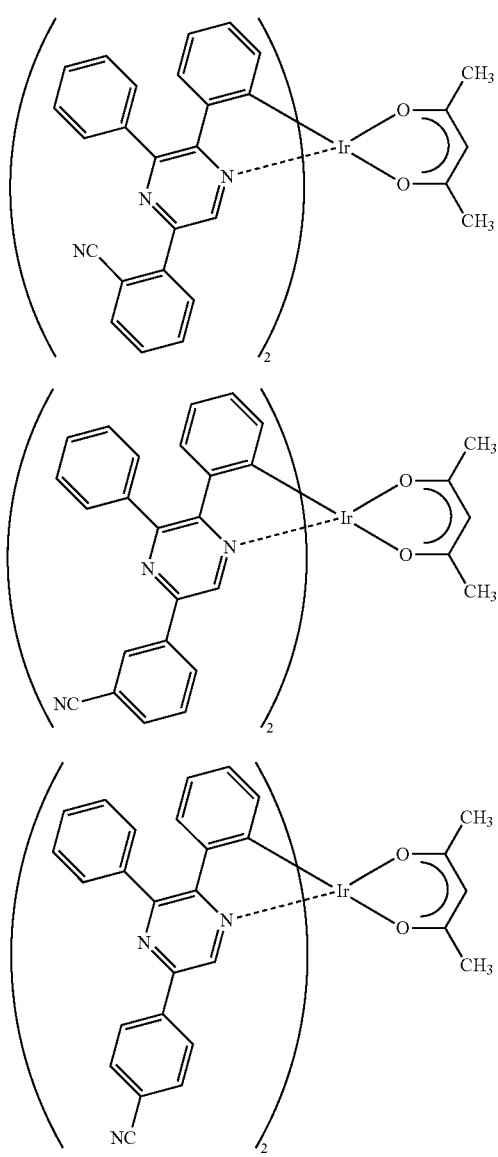

A pyrazine derivative represented by the following structural formula (G0-1), (G0-2), or (G0-3) is preferable as the pyrazine derivative represented by the above-mentioned general formula (G0) in terms of easiness of synthesizing an organometallic complex.

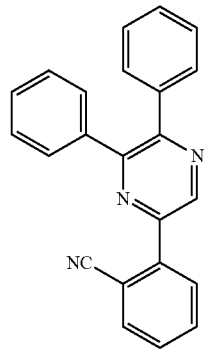

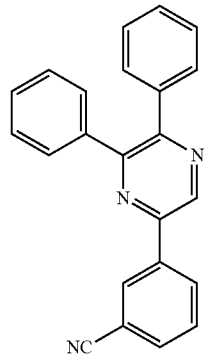

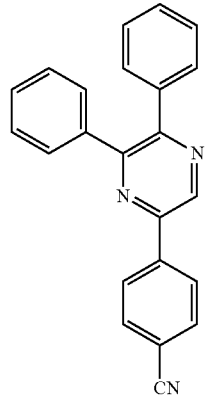

In an organometallic complex having the structure represented by any of the above-mentioned general formulae (G1) to (G5) and the above-mentioned structural formulae (1), (2), and (3), the coordinate structure in which the pyrazine derivative represented by the general formula (G0) is ortho-metalated with a metal ion, contributes to emission of phosphorescence greatly. Therefore, another embodiment of the present invention is a light-emitting material including such an organometallic complex as described above.

The organometallic complex of one embodiment of the present invention is highly effective in realizing higher efficiency in a case of being applied to a light-emitting element because the organometallic complex of the present invention is capable of emitting phosphorescence, that is, conversion of triplet excitation energy to luminescence. Therefore, a light-emitting element using any one of the above-mentioned organometallic complexes is also one embodiment of the present invention.

At this time, the organometallic complex of one embodiment of the present invention is effective in use for a light-emitting substance in terms of emission efficiency. Therefore, the light-emitting element in which an organometallic complex of one embodiment of the present invention is used for a light-emitting substance is also one embodiment of the present invention. Further, it is preferable that the light-emitting element includes a light-emitting layer between a pair of electrodes and the light-emitting layer has a structure in which the organometallic complex of one embodiment of the present invention is dispersed in the host material.

The thus obtained light-emitting element of one embodiment of the present invention can realize high emission efficiency, and thus a light-emitting device (such as an image display device or a light-emitting device) using this light-emitting element can realize low power consumption. Accordingly, a light-emitting device and an electronic device using the light-emitting element according to the present invention is also one embodiment of the present invention.

The light-emitting device of one embodiment of the present invention has a feature in which the light-emitting device includes a light-emitting layer between a pair of electrodes, and the light-emitting layer includes a light-emitting element containing the above-described organometallic complex and a control unit to control light emission from the light-emitting element. Note that the light-emitting device in this specification includes an image display device or a light-emitting device using the light-emitting element. Further, the category of the light-emitting device of the present invention includes a module including a substrate provided with a light-emitting element, attached with a connector, for example, a tape automated bonding (TAB) tape such as an anisotropic conductive film or a tape carrier package (TCP); a module in which an end of the connector is provided with a printed wiring board; or a module in which an integrated circuit (IC) is directly mounted on a substrate, provided with a light-emitting element, by a chip on glass (COG) method; and the like. Further, the category includes a light-emitting device used for lightning equipment or the like.

The electronic device of one embodiment of the present invention includes a display portion, which includes the above-mentioned light-emitting element and the control unit to control light emission from the light-emitting element.

The organometallic complex of one embodiment of the present invention can emit favorable red-color light. The organometallic complex of one embodiment of the present invention has a peak of light emission at about 620 nm. Further, the organometallic complex of one embodiment of the present invention has high emission efficiency. In addition, red-color light emission with high luminous efficiency (cd/A) can be obtained by an organometallic complex of one embodiment of the present invention.

Further, by manufacturing a light-emitting element with use of the organometallic complex of one embodiment of the present invention, a light-emitting element with high emission efficiency can be obtained. Furthermore, a light-emitting element that emits red-color light with high luminous efficiency can be obtained.

Further, by using the organometallic complex of one embodiment of the present invention, a light-emitting device and an electronic device with reduced power consumption can be provided. Furthermore, a light-emitting device and an electronic device which has high red color reproducibility and provides high quality images can be provided.

BRIEF DESCRIPTION OF THE DRAWINGS

In the accompany drawings:

FIGS. 4A and 4B illustrate a light-emitting device according to one embodiment of the present invention;

DETAILED DESCRIPTION OF THE INVENTION

Figure 1:
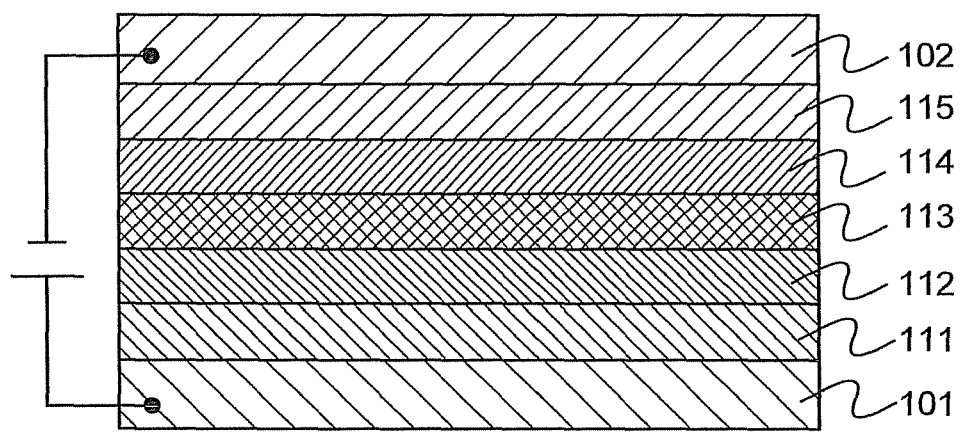
FIG. 1 illustrates a light-emitting element according to one embodiment of the present invention.

Embodiments of the invention disclosed below will be described in detail with reference to accompanying drawings. Note that the invention disclosed below is not limited to the following description because it will be easily understood by those skilled in the art that various changes and modifications can be made without departing from the spirit and scope of the present invention. Therefore, the present invention should not be interpreted as being limited to the following description of the embodiments.

Embodiment 1

An organometallic complex according to one embodiment of the present invention will be described in Embodiment 1.

<Synthesis Method of a Pyrazine Derivative Represented by the General Formula (G0)>

An organometallic complex of one embodiment of the present invention is formed by ortho metalation of a pyrazine derivative represented by the following general formula (G0) with a metal ion belonging to Group 9 or Group 10.

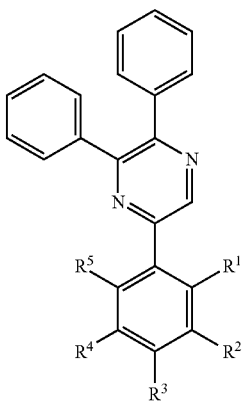

(G0)

In the formula, $R^1$ to $R^5$ each represent hydrogen or a cyano group, and at least one of $R^1$ to $R^5$ is a cyano group.

The pyrazine derivative represented by the general formula (G0) can be synthesized by the following simple and easy synthesis scheme. For example, as shown in the following synthesis scheme (a), the pyrazine derivative can be obtained by reacting a halogen compound of a pyrazine derivative (A1) with an arylboronic acid compound (A2). Note that in the synthesis scheme (a), X represents a halogen element. Further, $R^1$ to $R^5$ each represent hydrogen or a cyano group, and at least one of $R^1$ to $R^5$ is a cyano group.

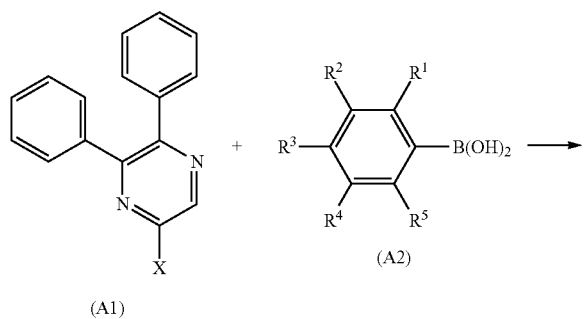

(a)

(A1)   (A2)

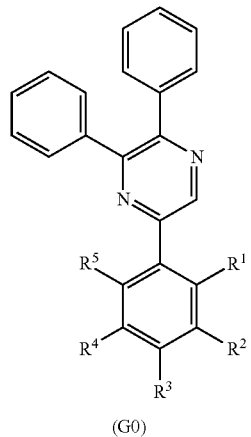

(G0)

Alternatively, as shown in the following synthesis scheme (a'), the pyrazine derivative can be obtained by reacting a pyrazine derivative (A1') with an aryllithium compound or an arylmagnesium bromide compound (A2'). Note that in the synthesis scheme (a'), $R^1$ to $R^5$ each represent hydrogen or a cyano group, and at least one of $R^1$ to $R^5$ is a cyano group.

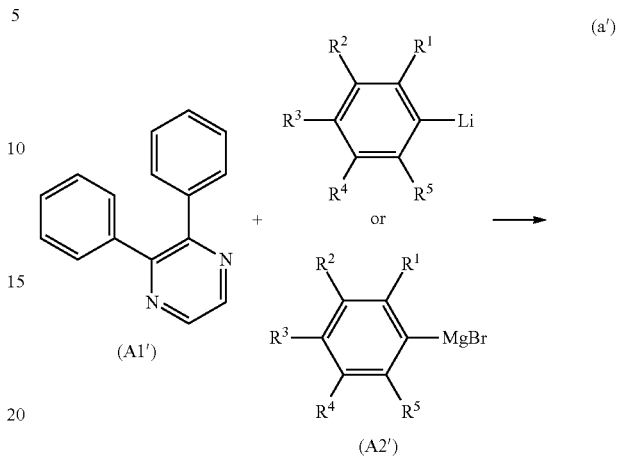

(a')

(A1')

(A2')

(G0)

Alternatively, as shown in the following synthesis scheme (a"), the pyrazine derivative can be obtained by reacting 1,2-diamino compound (A1") with 1,2-dicarbonyl compound (A2"). Note that in the synthesis scheme (a"), $R^1$ to $R^5$ each represent hydrogen or a cyano group, and at least one of $R^1$ to $R^5$ is a cyano group.

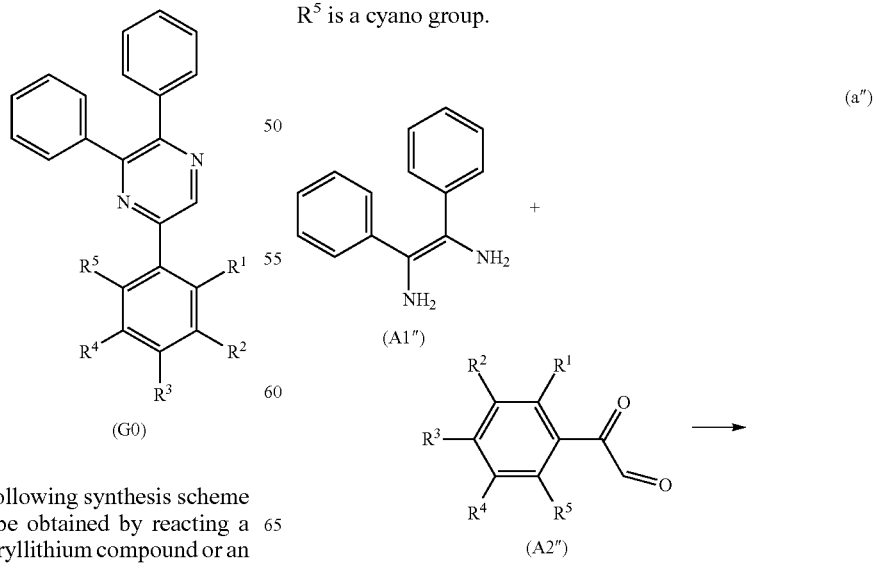

(a")

(A1")

(A2")

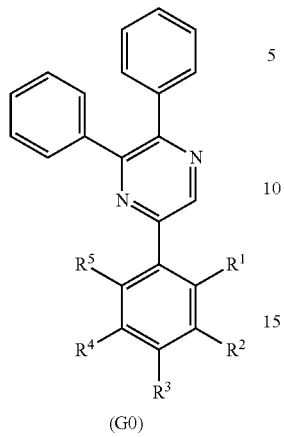

(G0)

<Synthesis Method of an Organometallic Complex of the Present Invention Represented by the General Formula (G2)>

Next, an organometallic complex represented by the following general formula (G2) will be described.

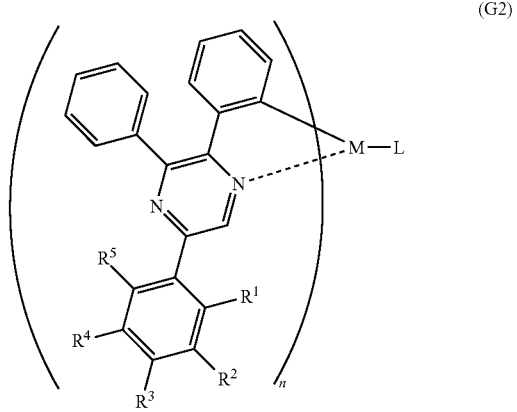

(G2)

In the formula, $R^1$ to $R^5$ each represent hydrogen or a cyano group, and at least one of $R^1$ to $R^5$ is a cyano group. Further, M represents a central metal which is an element belonging to Group 9 or Group 10. Furthermore, L represents a monoanionic ligand.

The organometallic complex represented by the general formula (G2) exhibits favorable red-color phosphorescence emission. In the general formula (G2), the partial structure (the structure represented by the following general formula (G1)) ortho-metalated with a metal ion belonging to Group 9 or Group 10 contributes to emission of phosphorescence greatly.

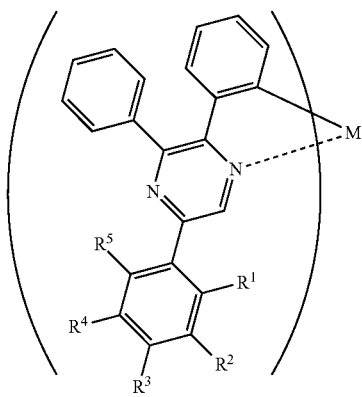

(G1)

In the formula, $R^1$ to $R^5$ each represent hydrogen or a cyano group, and at least one of $R^1$ to $R^5$ is a cyano group. Further, M represents a central metal which is an element belonging to Group 9 or Group 10.

Note that in the above-mentioned general formulae (G1) and (G2), a cyano group is preferably applied to any one of $R^1$ to $R^5$ in terms of easiness of synthesizing an organometallic complex.

Further, the monoanionic ligand L is preferably any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen, because these ligands have high coordinating ability. More preferably, the monoanionic ligand L is a monoanionic ligand represented by any of the following structural formulae (L1) to (L8). Since these ligands have high coordinating ability and can be obtained at low price, they are favorable.

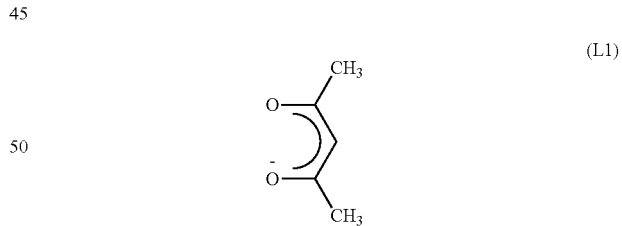

(L1)

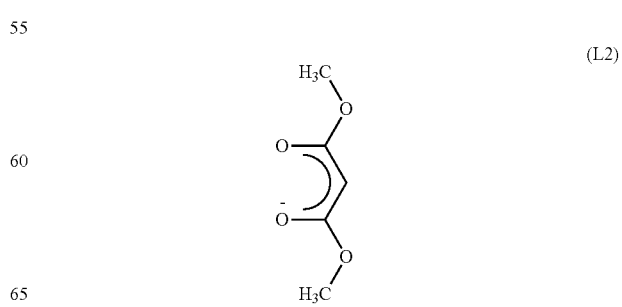

(L2)

(L3)
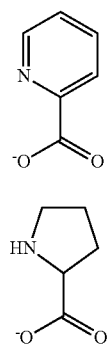

(L4)
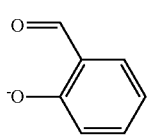

(L5)
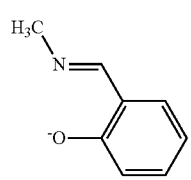

(L6)
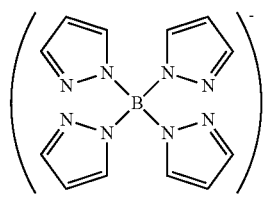

(L7)
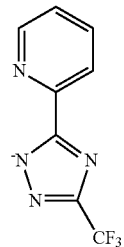

(L8)
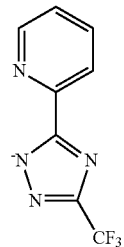

Note that the center metal M is selected from elements belonging to Group 9 or Group 10; however, iridium(III) or platinum(II) is preferable in terms of emission efficiency. In particular, iridium(III) is preferable since it is thermally stable.

First, as shown in the following synthesis scheme (b), the pyrazine derivative represented by the general formula (G0) and a compound of a metal belonging to Group 9 or Group 10 which contains halogen (such as a metal halide or a metal complex) are heated in an appropriate solvent, thereby a dinuclear complex (B) can be obtained which is a kind of organometallic complexes of the present invention and has the structure represented by the general formula (G1). As a compound of a metal belonging to Group 9 or Group 10 which contains halogen, rhodium chloride hydrate, palladium chloride, iridium chloride hydrate, iridium chloride hydrochloride hydrate, potassium tetrachloroplatinate(II) are given. Note that in the synthesis scheme (b), M represents an element belonging to Group 9 or Group 10, and X represents a halogen element. Further, n is 2 when M is an element belonging to Group 9, and n is 1 when M is an element belonging to Group 10.

(b)

Compound of Metal Belonging to Group 9 or Group 10 which Contains Halogen +

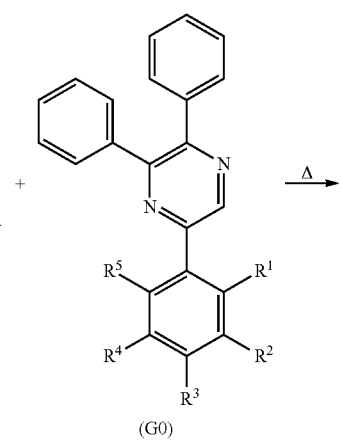

(G0)

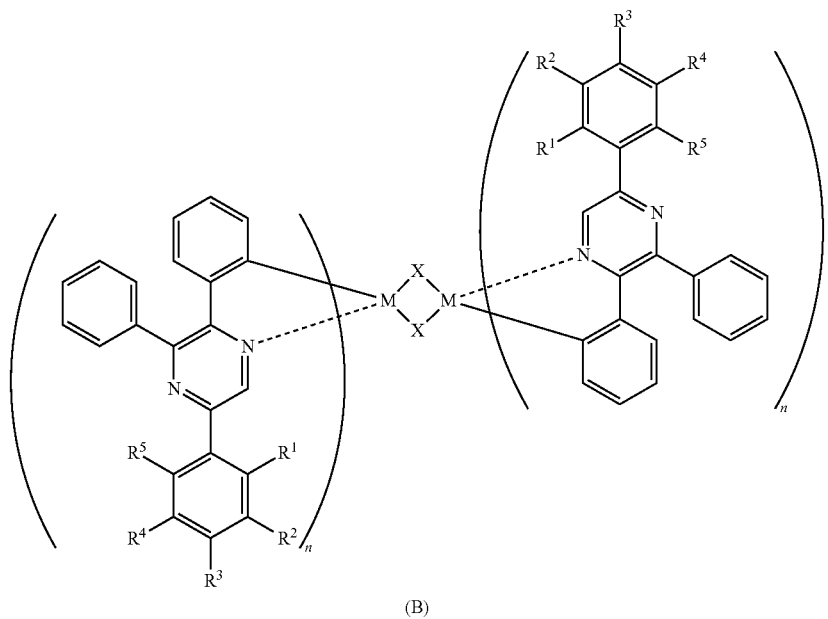

(B)

Next, the organometallic complex represented by the general formula (G2) can be obtained as follows: the dinuclear complex (B) obtained according to the above synthesis scheme (b) is reacted with HL (H means hydrogen) that is a material of a monoanionic ligand L, and a proton of HL is eliminated and coordinated to the central metal M. Note that in the synthesis scheme (c), M represents an element belonging to Group 9 or Group 10, and X represents a halogen element. Further, n is 2 when M is an element belonging to Group 9, and n is 1 when M is an element belonging to Group 10. Furthermore, L represents a monoanionic ligand.

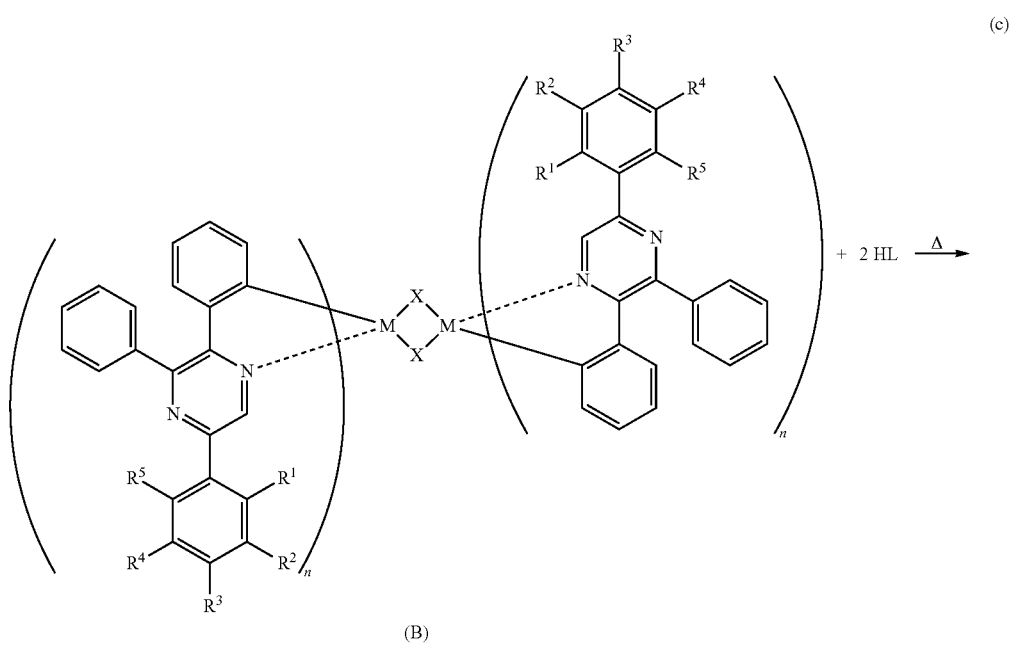

(B)

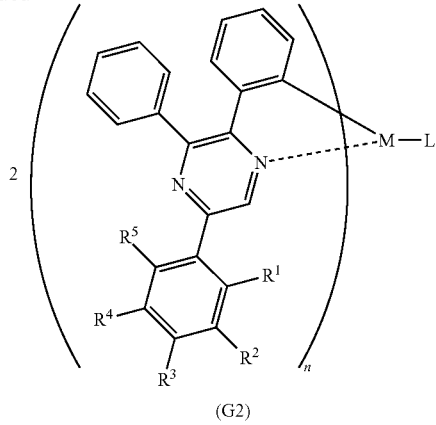

(G2)

Note that in the synthesis schemes (b) and (c), $R^1$ to $R^5$ each represent hydrogen or a cyano group, and at least one of $R^1$ to $R^5$ is a cyano group. A cyano group is preferably applied to any one of $R^1$ to $R^5$ in terms of easiness of synthesizing an organometallic complex.

Hereinafter, specific examples of organometallic complexes in Embodiment 1 are given (structural formulae (1) to (20)). However, the present invention is not limited to these.

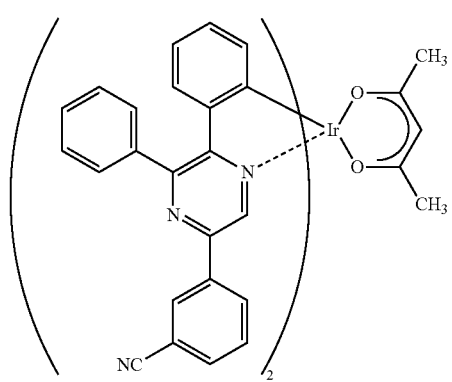

(1)

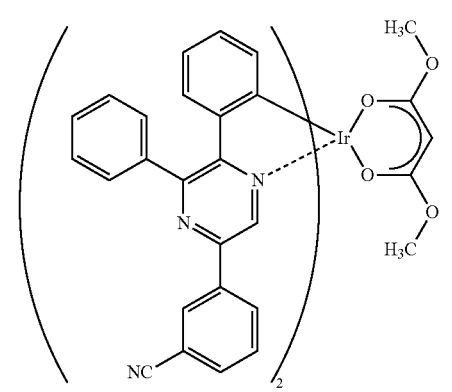

(2)

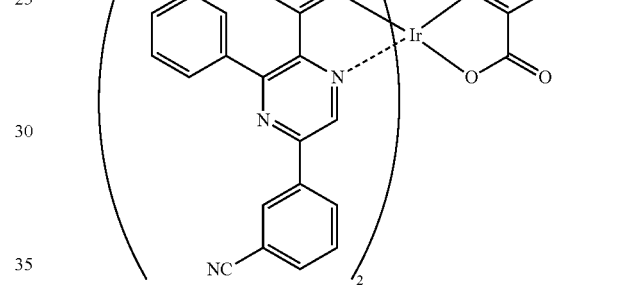

(3)

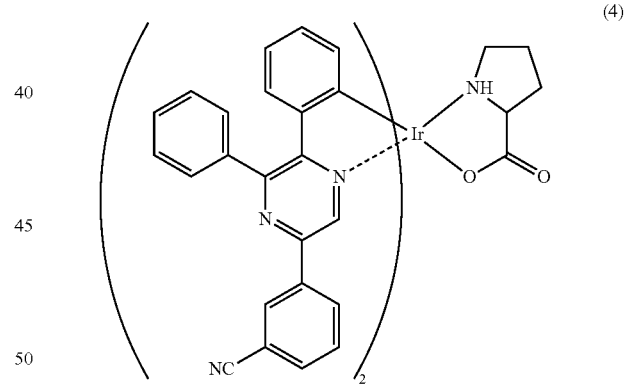

(4)

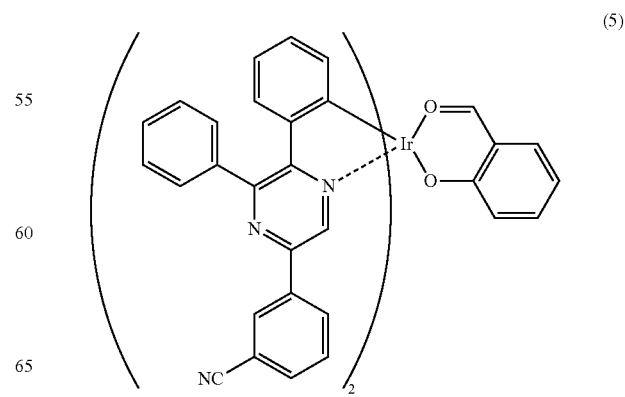

(5)

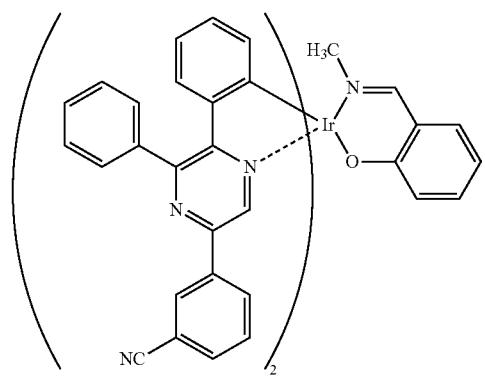
(6)
(7)
(8)
(9)
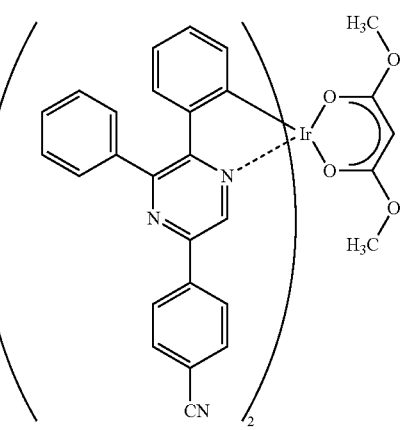
(10)
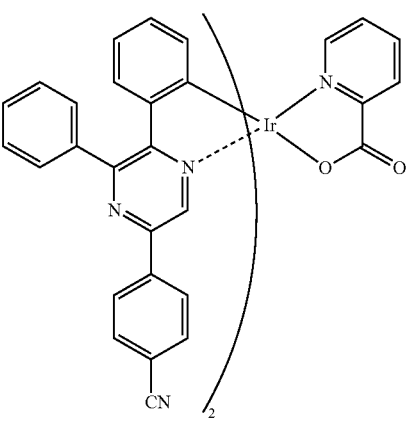
(11)
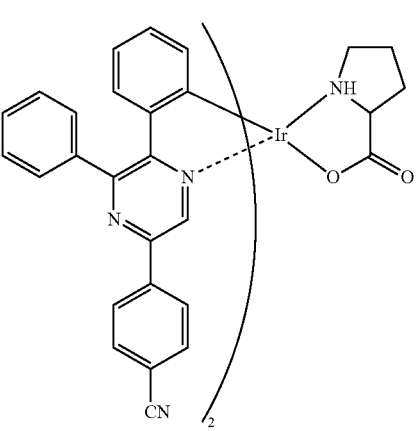
(12)

-continued
(13)
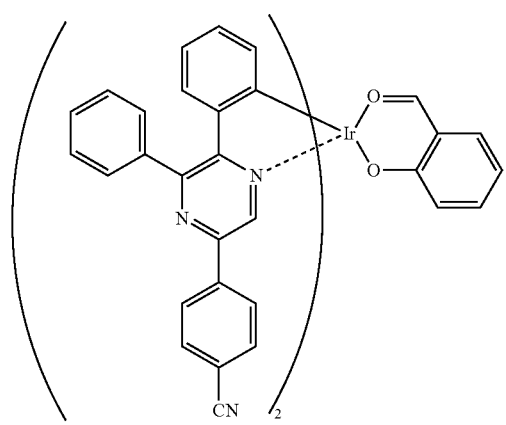
(14)
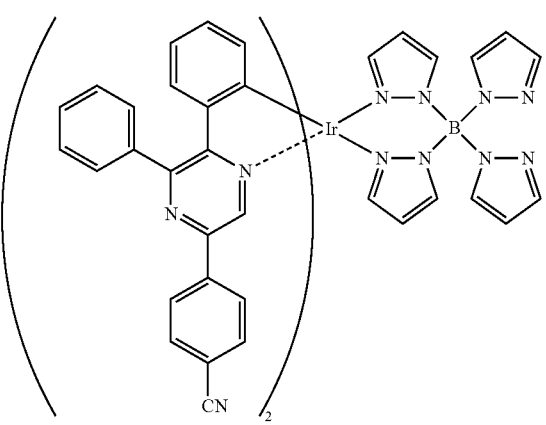
(15)
(16)
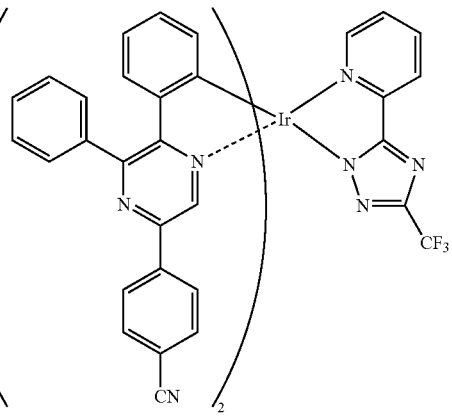
(17)
(18)
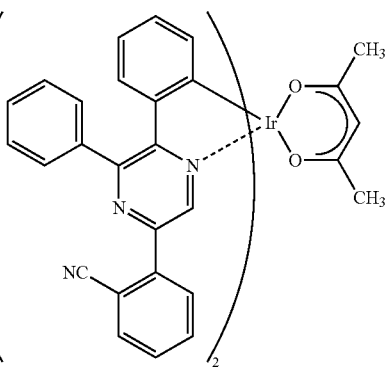
(19)
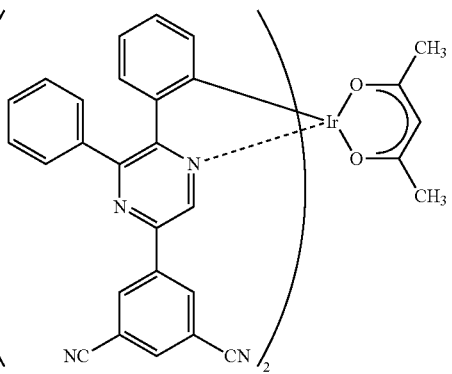

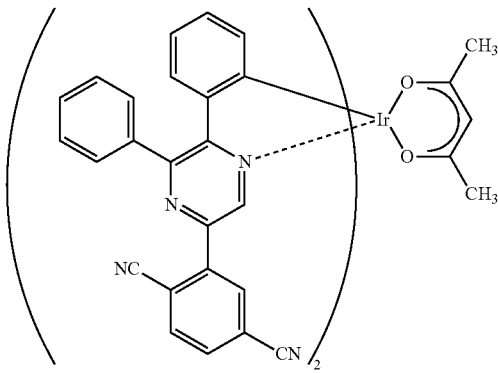

(20)

The above-described organometallic complexes each have a peak of light emission at about 620 nm and emit excellent red-color light with high luminous efficiency. Further, the organometallic complexes can be used as photosensitizers owing to their capability of intersystem crossing. Furthermore, the organometallic complexes can be applied as a light-emitting material or a light-emitting substance for a light-emitting element because the organometallic complexes are capable of emitting phosphorescence.

Embodiment 2

Embodiment 2 will describe an embodiment of a light-emitting element which includes any of the organometallic complexes described in Embodiment 1 as a light-emitting substance with reference to FIG. 1.

FIG. 1 illustrates a light-emitting element including a light-emitting layer 113 between a first electrode 101 and a second electrode 102. The light-emitting layer 113 includes any of the organometallic complexes of the present invention as described above in Embodiment 1.

By applying voltage to such a light-emitting element, holes injected from the first electrode 101 and electrons injected from the second electrode 102 are recombined with each other in the light-emitting layer 113 to bring any of the organometallic complexes described in Embodiment 1 to an excited state. Light is emitted when the organometallic complex in the excited state returns to the ground state. Any of the organometallic complexes described in Embodiment 1 thus functions as a light-emitting substance of the light-emitting element. Note that the first electrode 101 and the second electrode 102 function as an anode and a cathode, respectively, in the light-emitting element of Embodiment 2.

Here, the light-emitting layer 113 includes any of the organometallic complexes described in Embodiment 1. That is, the light-emitting layer 113 includes an organometallic complex having the structure represented by the general formula (G1), and more preferably, includes an organometallic complex represented by the general formula (G2). The light-emitting layer 113 preferably includes a substance that has larger triplet excitation energy than any of the organometallic complexes described in Embodiment 1 as a host, and includes any of the organometallic complexes described in Embodiment 1, which is dispersed as a guest. Thus, quenching of light emission from the organometallic complex caused depending on the concentration can be prevented. Note that the triplet excitation energy refers to an energy difference between a ground state and a triplet excited state.

Although there is no particular limitation on the substance used for dispersing any of the organometallic complexes described in Embodiment 1 (i.e., a host), preferable examples are given: a compound having an arylamine skeleton, such as 2,3-bis(4-diphenylaminophenyl)quinoxaline (abbreviation: TPAQn) or 4,4'-bis[N-(1-naphthyl)-N-phenylamino]biphenyl (abbreviation: NPB); a carbazole derivative such as 4,4'-di(N-carbazolyl)biphenyl (abbreviation: CBP) or 4,4',4''-tri(N-carbazolyl)triphenylamine (abbreviation: TCTA); and a metal complex such as bis[2-(2-hydroxyphenyl)pyridinato]zinc (abbreviation: Znpp$_2$), bis[2-(2-hydroxyphenyl)benzoxazolato]zinc (abbreviation: ZnBOX), bis(2-methyl-8-quinolinolato)(4-phenylphenolato)aluminum (abbreviation: BAlq) or tris(8-quinolinolato)aluminum (abbreviation: Alq$_3$). Further, a high molecular compound such as poly(N-vinylcarbazole) (abbreviation: PVK) can also be used. In particular, any of the organometallic complexes described in Embodiment 1 can emit light efficiently with use of a metal complex such as bis[2-(2-hydroxyphenyl)pyridinato]zinc (abbreviation: Znpp$_2$), bis[2-(2-hydroxyphenyl)benzoxazolato]zinc (abbreviation: ZnBOX), or bis(2-methyl-8-quinolinolato)(4-phenylphenolato)aluminum (abbreviation: BAlq). It is further preferable to use a zinc complex.

Note that because any of the organometallic complexes described in Embodiment 1 can emit favorable red-color light, a light-emitting element that emits red-color light can be obtained. Further, any of the organometallic complexes described in Embodiment 1 is capable of emitting phosphorescence, so that it has high emission efficiency. Thus, by using the organometallic complex for a light-emitting layer, a light-emitting element with high emission efficiency can be obtained. Furthermore, since the peak of light emission of the organometallic complex is about 620 nm, a light-emitting element that emits red-color light with high luminous efficiency (cd/A) can be obtained.

Since the light-emitting element described in Embodiment 2 has high emission efficiency, the power consumption can be reduced.

Although there is no particular limitation on the first electrode 101, it is preferably formed using a substance having a high work function in the case of functioning as an anode as in Embodiment 2. Specific examples of the substance having a high work function include gold (Au), platinum (Pt), nickel (Ni), tungsten (W), chromium (Cr), molybdenum (Mo), iron (Fe), cobalt (Co), copper (Cu), palladium (Pd) in addition to indium tin oxide (ITO), indium tin oxide containing silicon oxide (ITSO), and indium oxide containing zinc oxide at 2 to 20 wt % (IZO). Note that the first electrode 101 can be formed by, for example, a sputtering method or an evaporation method.

Further, although there is also no particular limitation on the second electrode 102, it is preferably formed of a substance having a low work function in the case of functioning as a cathode as in Embodiment 2. Specific examples of the substance having a low work function include an alkali metal such as lithium (Li) or cesium (Cs), an alkaline-earth metal such as magnesium (Mg) or calcium (Ca), and a rare-earth metal such as erbium (Er) or ytterbium (Yb), in addition to aluminum (Al) and indium (In). In addition, an alloy such as an aluminum-lithium alloy (AlLi) or a magnesium-silver alloy (MgAg) can be included. Note that the second electrode 102 can be formed by, for example, a sputtering method or an evaporation method.

In order to extract emitted light to the outside, it is preferable that one or both of the first electrode 101 and the second electrode 102 be an electrode formed using a conductive film that transmits visible light, such as ITO, or an electrode with a thickness of several nm to several tens of nm so as to transmit visible light.

A hole-transporting layer 112 may be provided between the first electrode 101 and the light-emitting layer 113 as illustrated in FIG. 1. Here, the hole-transporting layer refers to a layer that has a function of transporting holes injected from the first electrode 101 to the light-emitting layer 113. In this manner, the hole-transporting layer 112 is provided to keep the first electrode 101 away from the light-emitting layer 113; thus, quenching of light emission due to metal can be prevented. Note that the hole-transporting layer 112 is not necessarily provided.

Although there is no particular limitation on a substance forming the hole-transporting layer 112, for example, the following aromatic amine compounds are given: [N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), or 4,4',4"-tris[N-(3-methylphenyl)-N-phenylamino]triphenylamine (abbreviation: m-MTDATA). In addition, a high molecular compound such as poly(4-vinyltriphenylamine) (abbreviation: PVTPA) can also be used.

Note that the hole-transporting layer 112 may have a multilayer structure in which two or more layers are stacked, or may be formed of a mixture of two or more kinds of substances.

Further, an electron-transporting layer 114 may be provided between the second electrode 102 and the light-emitting layer 113 as illustrated in FIG. 1. Here, the electron-transporting layer refers to a layer that has a function of transporting electrons injected from the second electrode 102 to the light-emitting layer 113. In this manner, the electron-transporting layer 114 is provided to keep the second electrode 102 away from the light-emitting layer 113; thus, quenching of light emission due to a metal can be prevented. Note that the electron-transporting layer 114 is not necessarily provided.

Although there is no particular limitation on a substance forming the electron-transporting layer 114, for example, the following metal complexes are given: tris(8-quinolinolato)aluminum (abbreviation: $Alq_3$), tris(4-methyl-8-quinolinolato)aluminum (abbreviation: $Almq_3$), bis(10-hydroxybenzo[h]quinolinato)beryllium (abbreviation: $BeBq_2$), bis(2-methyl-8-quinolinolato)(4-phenylphenolato)aluminum (abbreviation: BAlq), bis[2-(2-hydroxyphenyl)benzoxazolato]zinc (abbreviation: ZnBOX), and bis[2-(2-hydroxyphenyl)benzothiazolato]zinc (abbreviation: $Zn(BTZ)_2$). Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. In addition, a high molecular compound such as poly(2,5-pyridine-diyl) (abbreviation: PPy) can also be used.

Note that the electron-transporting layer 114 may have a multilayer structure in which two or more layers are stacked, or may be formed of a mixture of two or more kinds of substances.

Further, a hole-injecting layer 111 may be provided between the first electrode 101 and the hole-transporting layer 112 as illustrated in FIG. 1. Here, the hole-injecting layer refers to a layer that has a function of assisting injection of holes from the electrode functioning as an anode into the hole-transporting layer 112. Note that the hole-injecting layer 111 is not necessarily provided.

Although there is no particular limitation on a substance forming the hole-injecting layer 111, for example, the following metal oxides can be used: vanadium oxide, niobium oxide, tantalum oxide, chromium oxide, molybdenum oxide, tungsten oxide, manganese oxide, rhenium oxide, or ruthenium oxide. Further, a phthalocyanine compound such as phthalocyanine (abbreviation: $H_2Pc$) or copper phthalocyanine (abbreviation: CuPc) can be used. Furthermore, the substances used for forming the hole-transporting layer 112 as described above can also be used. Moreover, a high molecular compound such as a mixture of poly(ethylenedioxythiophene) and poly(styrenesulfonic acid) (abbreviation: PEDOT/PSS) can also be used.

A composite material of an organic compound and an electron acceptor may be used for the hole-injecting layer 111. Such a composite material is superior in a hole-injecting property and a hole-transporting property since holes are generated in the organic compound by the electron acceptor. In this case, the organic compound is preferably a material excellent in transporting the generated holes. Specifically, the above-mentioned substances forming the hole-transporting layer 112 (e.g., an aromatic amine compound) can be used, for example. As the electron acceptor, a substance having an electron accepting property to the organic compound may be used. Specifically, transition metal oxide is preferable and examples thereof include vanadium oxide, niobium oxide, tantalum oxide, chromium oxide, molybdenum oxide, tungsten oxide, manganese oxide, rhenium oxide, ruthenium oxide. Lewis acid such as iron(III) chloride or aluminum(III) chloride can also be used. In addition, an organic compound such as 7,7,8,8-tetracyano-2,3,5,6-tetrafluoroquinodimethane (abbreviation: F4-TCNQ) can also be used.

Note that the hole-injecting layer 111 may have a multilayer structure in which two or more layers are stacked, or may be formed of a mixture of two or more kinds of substances.

Further, an electron-injecting layer 115 may be provided between the second electrode 102 and the electron-transporting layer 114 as illustrated in FIG. 1. Here, the electron-injecting layer refers to a layer that has a function of assisting injection of electrons from the electrode functioning as a cathode into the electron-transporting layer 114. Note that the electron-injecting layer 115 is not necessarily provided.

Although there is no particular limitation on a substance forming the electron-injecting layer 115, for example, an alkali metal compound or an alkaline-earth metal compound such as lithium fluoride (LiF), cesium fluoride (CsF), calcium fluoride ($CaF_2$), or lithium oxide ($LiO_x$) can be used. In addition, a rare-earth metal compound such as erbium fluoride ($ErF_3$) can also be used. The above-mentioned substances forming the electron-transporting layer 114 can also be used.

A composite material of an organic compound and an electron donor may be used for the electron-injecting layer 115. Such a composite material is excellent in an electron-injecting property and an electron-transporting property since electrons are generated in the organic compound by the electron donor. In this case, the organic compound is preferably a material excellent in transporting the generated electrons. Specifically, the above-mentioned substances forming the electron-transporting layer 114 (e.g., a metal complex or a heteroaromatic compound) can be used, for example. As the electron donor, a substance having an electron-donating property to the organic compound may be used. Specifically, an alkali metal, an alkaline-earth metal, and a rare-earth metal are preferable and examples thereof include lithium, cesium, magnesium, calcium, erbium, and ytterbium. Further, alkali metal oxide and alkaline-earth metal oxide are preferable and examples thereof include lithium oxide ($LiO_x$), calcium oxide ($CaO_x$), and barium oxide ($BaO_x$). Lewis base such as magnesium oxide can also be used. Furthermore, an organic compound such as tetrathiafulvalene (abbreviation: TTF) can also be used.

In the light-emitting element described in Embodiment 2, each of the hole-injecting layer 111, the hole-transporting layer 112, the light-emitting layer 113, the electron-transporting layer 114, and the electron-injecting layer 115 may be formed by an evaporation method, an ink-jet method, a coating method, or the like. In addition, each of the first electrode 101 and the second electrode 102 may also be formed by a sputtering method, an evaporation method, an ink-jet method, a coating method, or the like.

Embodiment 3

In Embodiment 3, an embodiment of a light-emitting element different from that in Embodiment 2 will be described with reference to FIG. 2. The embodiment of a light-emitting element using any of the organometallic complexes described in Embodiment 1 may have a plurality of light-emitting layers. The plurality of light-emitting layers is provided and then each of them emits light. Accordingly, light that is a combination of light emitted from the plurality of light-emitting layers can be obtained; for example, white-color light can be obtained. In Embodiment 3, an embodiment of a light-emitting element including a plurality of light-emitting layers will be described with reference to FIG. 2.

Figure 2:
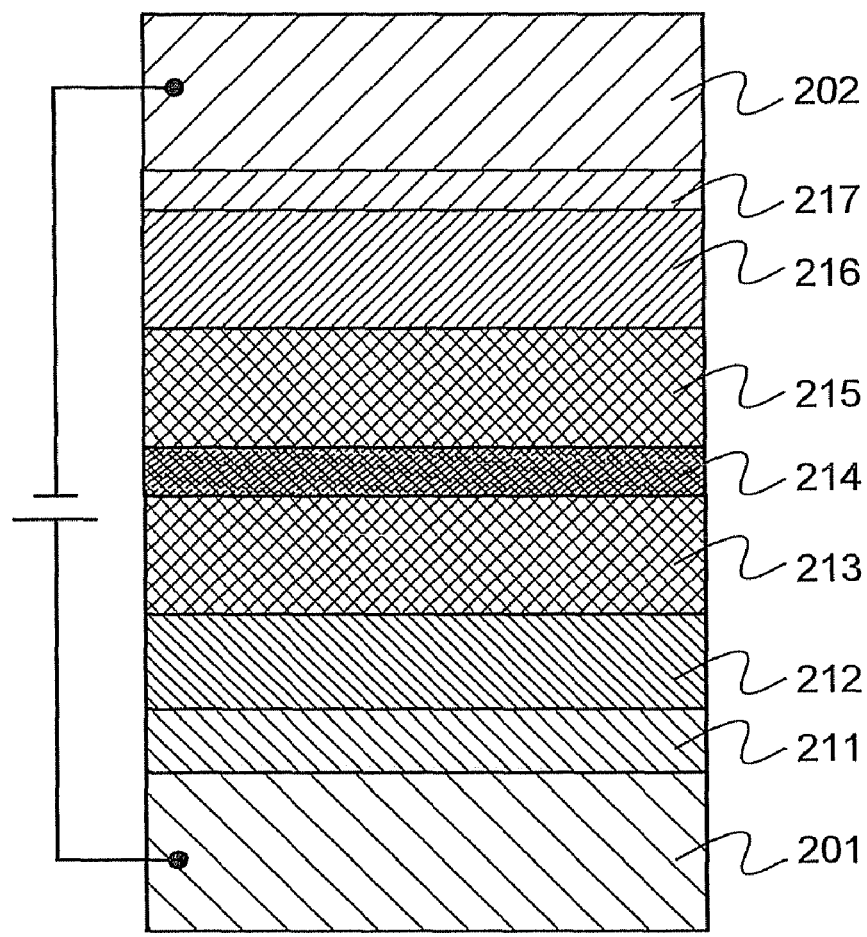
FIG. 2 illustrates a light-emitting element according to one embodiment of the present invention.

In FIG. 2, a first light-emitting layer 213 and a second light-emitting layer 215 are provided between a first electrode 201 and a second electrode 202. Light that is a combination of light emitted from the first light-emitting layer 213 and light emitted from the second light-emitting layer 215 can be obtained. A separation layer 214 is preferably formed between the first light-emitting layer 213 and the second light-emitting layer 215.

When voltage is applied so that the potential of the first electrode 201 is higher than that of the second electrode 202, current flows between the first electrode 201 and the second electrode 202, and holes and electrons are recombined with each other in the first light-emitting layer 213, the second light-emitting layer 215, or the separation layer 214. The generated excitation energy is distributed to the first light-emitting layer 213 and the second light-emitting layer 215 to bring each of a first light-emitting substance contained in the first light-emitting layer 213 and a second light-emitting substance contained in the second light-emitting layer 215 to an excited state. Then, the first substance and the second light-emitting substance in the excited state each emit light when returning to the ground state.

The first light-emitting layer 213 includes the first light-emitting substance typified by a fluorescent compound such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(N-ethylcarbazol-3-yl)vinyl]biphenyl (abbreviation: BCzVBi), bis(2-methyl-8-quinolinolato)(4-phenylphenolato)aluminum (abbreviation: BAlq), or bis(2-methyl-8-quinolinolato)galliumchloride (abbreviation: $Gamq_2Cl$); or a phosphorescent compound such as bis{2-[3,5-bis(trifluoromethyl)phenyl]pyridinato-$N,C^{2'}$}iridium(III) picolinate (abbreviation: $Ir(CF_3ppy)_2(pic)$), bis[2-(4,6-difluorophenyl)pyridinato-$N,C^{2'}$]iridium(III)acetylacetonate (abbreviation: FIr(acac)), bis[2-(4,6-difluorophenyl)pyridinato-$N,C^{2'}$]iridium(III)picolinate (abbreviation: FIrpic), or bis[2-(4,6-difluorophenyl)pyridinato-$N,C^{2'}$]iridium(III)tetra (1-pyrazolyl)borate (abbreviation: $FIr_6$), by which light emission with a peak of emission spectrum at 450 nm to 510 nm (i.e., blue light to blue green light) can be obtained. When the first light-emitting substance is a fluorescent compound, the first light-emitting layer 213 may preferably have a structure in which a substance having larger singlet excitation energy than the first light-emitting substance is used as a first host and the first light-emitting substance is dispersed as a guest. Alternatively, when the first light-emitting substance is a phosphorescent compound, the first light-emitting layer 213 preferably has a structure in which a substance having larger triplet excitation energy than the first light-emitting substance is used as a first host and the first light-emitting substance is dispersed as a guest. As the first host, 9,10-di(2-naphthyl) anthracene (abbreviation: DNA), 2-tert-butyl-9,10-di(2-naphthyl)anthracene (abbreviation: t-BuDNA) or the like can be used in addition to NPB, CBP, TCTA, or the like that are described above. Note that the singlet excitation energy refers to an energy difference between a ground state and a singlet excited state, and the triplet excitation energy refers to an energy difference between a ground state and a triplet excited state.

On the other hand, the second light-emitting layer 215 includes any of the organometallic complexes described in Embodiment 1 and emits red-color light. Further, since any of the organometallic complexes described in Embodiment 1 has high emission efficiency, a light-emitting element with high emission efficiency can be obtained. Furthermore, a light-emitting element with low power consumption can be obtained.

The second light-emitting layer 215 may have a structure similar to the light-emitting layer 113 described in Embodiment 2.

The separation layer 214 can be formed, specifically, using TPAQn, NPB, CBP, TCTA, $Znpp_2$, ZnBOX, or the like, which are described above. The separation layer 214 is provided in this manner, and therefore a defect that emission intensity of one of the first light-emitting layer 213 and the second light-emitting layer 215 is stronger than that of the other thereof can be prevented. However, the separation layer 214 is not necessarily provided, and it may be provided as appropriate such that the ratio between emission intensities of the first light-emitting layer 213 and the second light-emitting layer 215 can be adjusted.

Note that in Embodiment 3, any of the organometallic complexes described in Embodiment 1 is used for the second light-emitting layer 215 and another light-emitting substance is used for the first light-emitting layer 213, whereas any of the organometallic complexes described in Embodiment 1 may be used for the first light-emitting layer 213 and another light-emitting substance may be used for the second light-emitting layer 215.

In Embodiment 3, a light-emitting element including two light-emitting layers as illustrated in FIG. 2 is described; however, the number of light-emitting layers is not limited to two, and may be more than two, for example may be three as long as light emissions from the light-emitting layers are mixed. As a result, white-color light with good color rendering properties can be obtained, for example.

The first electrode 201 may have a structure similar to the first electrode 101 described above in Embodiment 2. The second electrode 202 may also have a structure similar to the second electrode 102 described above in Embodiment 2.

In Embodiment 3, as illustrated in FIG. 2, a hole-injecting layer 211, a hole-transporting layer 212, an electron-transporting layer 216, and an electron-injecting layer 217 are provided. As to structures of these layers, the structures of the respective layers described above in Embodiment 2 may be applied. Note that these layers are not necessarily provided and may be provided depending on the element characteristics.

Embodiment 4

Embodiment 4 will exemplify a light-emitting element in which a plurality of light-emitting layers is provided and light is emitted from each of these layers with a different element structure from that in Embodiment 2 or Embodiment 3. Therefore, also in Embodiment 4, light that is a combination of light emitted from a plurality of light-emitting layers can be obtained; that is, white-color light can be obtained, for example. Hereinafter, explanation will be made with reference to FIG. 3.

Figure 3:
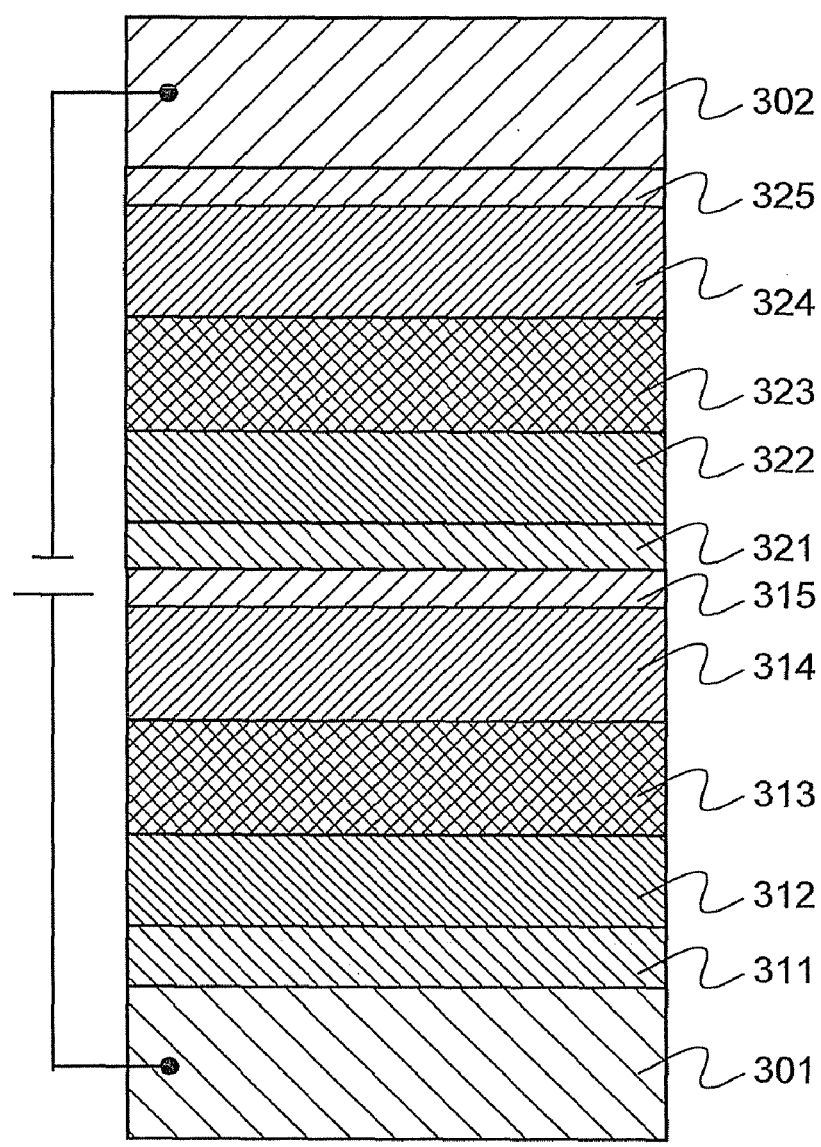
FIG. 3 illustrates a light-emitting element according to one embodiment of the present invention.

In the light-emitting element of FIG. 3, a first light-emitting layer 313 and a second light-emitting layer 323 are provided between a first electrode 301 and a second electrode 302. An N layer 315 and a P layer 321 are provided as charge generating layers between the first light-emitting layer 313 and the second light-emitting layer 323.

The N layer 315 generates electrons, and the P layer 321 generates holes. When voltage is applied such that the potential of the first electrode 301 is higher than that of the second electrode 302, holes injected from the first electrode 301 and electrons injected from the N layer 315 are recombined with each other in the first light-emitting layer 313, and thus, a first light-emitting substance contained in the first light-emitting layer 313 emits light. Further, electrons injected from the second electrode 302 and holes injected from the P layer 321 are recombined with each other in the second light-emitting layer 323, and thus, a second light-emitting substance contained in the second light-emitting layer 323 emits light.

The first light-emitting layer 313 may have a structure similar to the first light-emitting layer 213 in Embodiment 3, and light with a peak of emission spectrum at 450 nm to 510 nm (i.e., blue light to blue green light) can be obtained. The second light-emitting layer 323 may have a structure similar to the second light-emitting layer 215 in Embodiment 3, includes any of the organometallic complexes described in Embodiment 1 and emits red-color light. Since any of the organometallic complexes described in Embodiment 1 has high emission efficiency, a light-emitting element with high emission efficiency can be obtained. Further, a light-emitting element with low power consumption can be obtained.

Since the N layer 315 generates electrons, it may be formed using the composite material of the organic compound and the electron donor described in Embodiment 2. With such a structure, electrons can be injected to the first light-emitting layer 313 side.

Since the P layer 321 generates holes, it may be formed using the composite material of the organic compound and the electron acceptor described in Embodiment 2. With such a structure, holes can be injected to the second light-emitting layer 323 side. For the P layer 321, metal oxide having an excellent hole-injecting property, such as molybdenum oxide, vanadium oxide, ITO, or ITSO, can be used.

In Embodiment 3, a light-emitting element including two light-emitting layers as illustrated in FIG. 3 is described; however, the number of light-emitting layers is not limited to two, and may be more than two, for example may be three as long as light from each light-emitting layer is mixed. As a result, white-color emission with good color rendering properties can be obtained, for example.

Note that the first electrode 301 may have a structure similar to the first electrode 101 described above in Embodiment 2. The second electrode 302 may also have a structure similar to the second electrode 102 described above in Embodiment 2.

In Embodiment 4, as illustrated in FIG. 3, a hole-injecting layer 311, hole-transporting layers 312 and 322, electron-transporting layers 314 and 324, and an electron-injecting layer 325 are provided. As to structures of these layers, the structures of the respective layers described above in Embodiment 2 may also be applied. However, these layers are not necessarily provided and may be provided as appropriate depending on the element characteristics.

Embodiment 5

In Embodiment 5, an embodiment of a light-emitting element including any of the organometallic complexes described in Embodiment 1 as a sensitizer will be described with reference to FIG. 1.

FIG. 1 illustrates the light-emitting element including the light-emitting layer 113 between the first electrode 101 and the second electrode 102. The light-emitting layer 113 includes an organometallic complex as described above in Embodiment 1, and a fluorescent compound that can emit light with a longer wavelength than the organometallic complex.

In such a light-emitting element, holes injected from the first electrode 101 and electrons injected from the second electrode 102 are recombined with each other in the light-emitting layer 113 to bring the fluorescent compound to an excited state. Then, light is emitted when the fluorescent compound in the excited state returns to the ground state. At this time, any of the organometallic complexes described in Embodiment 1 acts as a sensitizer for the fluorescent compound to make more molecules of the fluorescent compound be in the singlet excited state. In this manner, a light-emitting element with excellent emission efficiency can be obtained by using any of the organometallic complexes described in Embodiment 1 as a sensitizer. Note that in the light-emitting element of Embodiment 5, the first electrode 101 and the second electrode 102 function as an anode and as a cathode, respectively.

The light-emitting layer 113 includes any of the organometallic complexes described in Embodiment 1 and the fluorescent compound that can emit light with a longer wavelength than the organometallic complex. The light-emitting layer 113 preferably has a structure in which a substance having larger triplet excitation energy than any of the organometallic complexes described in Embodiment 1 and larger singlet excitation energy than the fluorescent compound is used as a host, and any of the organometallic complexes described in Embodiment 1 and the fluorescent compound are dispersed as a guest.

There is no particular limitation on the substance used for dispersing any of the organometallic complexes described in Embodiment 1 and the fluorescent compound (i.e., host), and the substances given above as examples of the host in Embodiment 2, or the like can be used.

Although there is also no particular limitation on the fluorescent compound, a preferable example thereof is a compound that emits red light to infrared light, such as 4-dicyanomethylene-2-isopropyl-6-[2-(1,1,7,7- tetramethyljulolidin-9-yl)ethenyl]-4H-pyran (abbreviation: DCJTI), magnesium phthalocyanine, magnesium porphyrin, phthalocyanine.

Note that the first electrode 101 and the second electrode 102 may have structures similar to those of the first electrode and the second electrode, respectively, described above in Embodiment 2.

In Embodiment 5, as illustrated in FIG. 1, the hole-injecting layer 111, the hole-transporting layer 112, the electron-transporting layer 114, and the electron-injecting layer 115 are provided. As to structures of these layers, the structures of the respective layers described above in Embodiment 2 may be applied. Note that these layers are not necessarily needed and may be provided as appropriate depending on the element characteristics.

Light emission with high efficiency can be obtained from the above-described light-emitting element by using any of the organometallic complexes described in Embodiment 1 as a sensitizer.

Embodiment 6

In Embodiment 6, a light-emitting device manufactured using any of the organometallic complexes described in Embodiment 1 will be described with reference to FIGS. 4A and 4B. FIG. 4A is a top view of the light-emitting device, and FIG. 4B is a cross-sectional view of FIG. 4A taken along a line A-A' and a line B-B'. Reference numeral 601 denotes a driver circuit portion (source side driver circuit); 602 denotes a pixel portion; and 603 denotes a driver circuit portion (gate side driver circuit), which are indicated by dotted lines. Reference numeral 604 denotes a sealing substrate; 605 denotes a sealing material; and 607 denotes a space surrounded by the sealing material 605.

A lead wiring 608 is a wiring to transmit signals to be inputted to the source side driver circuit 601 and the gate side driver circuit 603, and receives a video signal, a clock signal, a start signal, a reset signal, and the like from a flexible printed circuit (FPC) 609 which serves as an external input terminal. Note that, although only an FPC is illustrated here, this FPC may be provided with a printed wiring board (PWB). The light-emitting device in this specification includes, in its category, not only a light-emitting device itself but also a light-emitting device provided with an FPC or a PWB.

Next, a cross-sectional structure will be described with reference to FIG. 4B. Although the driver circuit portions and the pixel portion are formed over an element substrate 610, the source side driver circuit 601 in the driver circuit portion and one pixel in the pixel portion 602 are illustrated here.

A CMOS circuit that is a combination of an n-channel TFT 623 and a p-channel TFT 624 is formed as the source side driver circuit 601. Each driver circuit portion may be any one of various circuits such as a CMOS circuit, a PMOS circuit, and an NMOS circuit. Although a driver integration type in which a driver circuit is formed over a substrate is described in Embodiment 6, a driver circuit is not necessarily formed over a substrate and can be formed outside a substrate.

The pixel portion 602 includes the plurality of pixels, each of which includes a switching TFT 611, a current control TFT 612, and a first electrode 613 which is electrically connected to the drain of the current control TFT 612. Note that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in the case of using a positive photosensitive acrylic as a material for the insulator 614, the insulator 614 is preferably formed so as to have a curved surface with a curvature radius (0.2 µm to 3 µm) only at the upper end portion thereof. Either a negative type that becomes insoluble in an etchant by light or a positive type that becomes soluble in an etchant by light can be used as the insulator 614.

A light-emitting layer 616 and a second electrode 617 are formed over the first electrode 613. Here, a material having a high work function is preferable as a material used for the first electrode 613 to serve as an anode. For example, the first electrode 613 can be formed using a stacked layer of a titanium nitride film and a film containing aluminum as its main component; a three-layer structure of a titanium nitride film, a film containing aluminum as its main component, and another titanium nitride film; or the like, as well as a single-layer film such as an ITO film, an indium tin oxide film containing silicon, an indium oxide film containing zinc oxide of 2 wt % to 20 wt %, a titanium nitride film, a chromium film, a tungsten film, a Zn film, or a Pt film. When the first electrode 613 has a stacked-layer structure, it can have low resistance as a wiring, form a favorable ohmic contact, and further function as an anode.

The light-emitting layer 616 is formed by various methods such as an evaporation method using an evaporation mask, an ink-jet method, or a spin coating method. The light-emitting layer 616 includes any of the organometallic complexes described in Embodiment 1. Further, the light-emitting layer 616 may include another material such as a low molecular material, an oligomer, a dendrimer, or a high molecular material.

As a material used for the second electrode 617 formed over the light-emitting layer 616 and serves as a cathode, a material having a low work function (Al, Mg, Li, Ca, or an alloy or a compound of them, such as MgAg, MgIn, AlLi, LiF, or $CaF_2$) is preferably used. In the case where light emitted from the light-emitting layer 616 is transmitted through the second electrode 617, a stacked layer of a metal thin film with reduced film thickness and a transparent conductive film (ITO, an indium oxide containing zinc oxide of 2 wt % to 20 wt %, an indium tin oxide containing silicon, zinc oxide (ZnO), or the like) is preferably used as the second electrode 617.

Attachment of the sealing substrate 604 to the element substrate 610 with the sealing material 605 makes a structure in which a light-emitting element 618 is provided in the space 607 surrounded by the element substrate 610, the sealing substrate 604, and the sealing material 605. Note that the space 607 is filled with filler, and there is a case where the space 607 is filled with the sealing material 605 as well as a case where the space 607 is filled with an inert gas (e.g., nitrogen or argon).

Note that an epoxy-based resin is preferably used as the sealing material 605. The material desirably allows as little moisture and oxygen as possible to penetrate. As the sealing substrate 604, a plastic substrate made of fiberglass-reinforced plastics (FRP), polyvinyl fluoride (PVF), polyester, an acrylic, or the like can be used besides a glass substrate or a quartz substrate.

In the above-described manner, a light-emitting device manufactured using any of the organometallic complexes described in Embodiment 1 can be obtained.

The light-emitting device of Embodiment 6 includes any of the organometallic complexes described in Embodiment 1; therefore, a light-emitting device having favorable characteristics can be obtained. Specifically, since the light-emitting element with high emission efficiency is included, a light-emitting device with low power consumption can be obtained. Further, since red-color light emission with high luminous efficiency can be realized, a light-emitting device with low power consumption and excellent color reproducibility, which is suitable for a full-color display, can be obtained.

Figure 5:
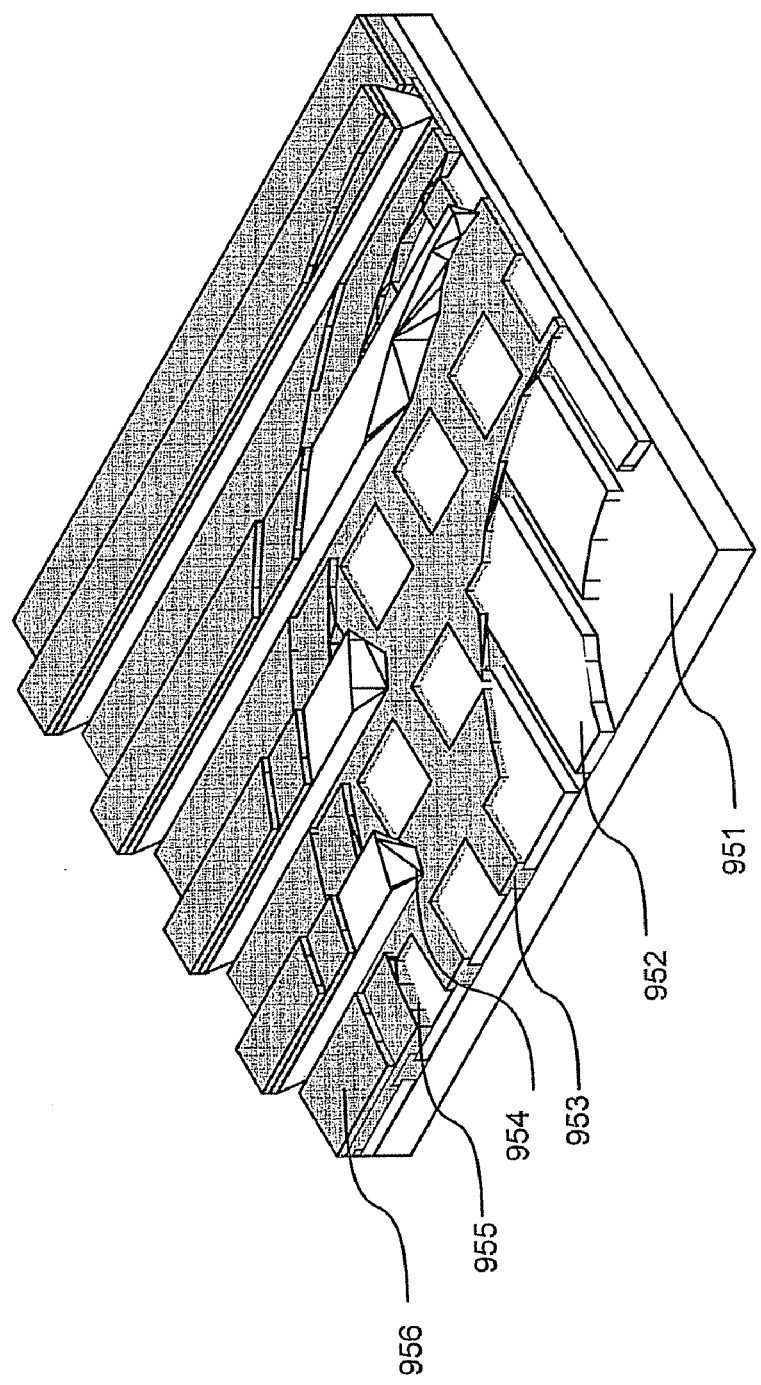
FIG. 5 illustrates a light-emitting device according to one embodiment of the present invention.

Although, as described above, description is made of an active matrix light-emitting device that controls driving of a light-emitting element with transistors, a passive matrix light-emitting device may be employed. FIG. 5 is a perspective view of a passive matrix light-emitting device manufactured according to the present invention. In FIG. 5, an electrode 952 and an electrode 956 are provided over a substrate 951, and a light-emitting layer 955 is provided therebetween. An end portion of the electrode 952 is covered with an insulating layer 953. A partition layer 954 is provided over the insulating layer 953. Sidewalls of the partition layer 954 slope so that a distance between one sidewall and the other sidewall becomes narrower toward a substrate surface. That is, a cross-section of the partition layer 954 in the direction of a short side is trapezoidal, and a base (side that is provided in the same direction as a plane direction of the insulating layer 953 and in contact with the insulating layer 953) is shorter than the upper side (side that is provided in the same direction as the plane direction of the insulating layer 953 and not in contact with the insulating layer 953). By providing the partition layer 954 in this manner, a defect of the light-emitting element caused by static electricity can be prevented. The passive matrix light-emitting device can also be driven with low power consumption when it includes a light-emitting element of the present invention having high emission efficiency.

Embodiment 7

In Embodiment 7, electronic devices each including the light-emitting device described in Embodiment 6 will be described. The electronic devices described in Embodiment 7 each include any of the organometallic complexes described in Embodiment 1 to include a display portion with high emission efficiency and low power consumption. Further, the electronic devices each include a display portion having excellent color reproducibility. In the case where any of the organometallic complexes described in Embodiment 1 is used for a full-color display, various light-emitting substances can be used and light-emitting elements having a structure similar to that described in Embodiments 2 to 5 can be employed for light-emitting elements of colors other than red color.

As an example of electronic devices including the light-emitting element manufactured using any of the organometallic complexes described in Embodiment 1, the following electronic devices are given: video cameras, digital cameras, goggle type displays, navigation systems, audio reproducing devices (e.g., car audio components and audio components), computers, game machines, portable information terminals (e.g., mobile computers, cellular phones, portable game machines, and electronic books), and image reproducing devices provided with a recording medium (specifically, devices capable of reproducing a recording medium such as a digital versatile disc (DVD) and provided with a display device that can display the image). Specific examples of these electronic devices are illustrated in FIGS. 6A to 6D.

Figure 6A:
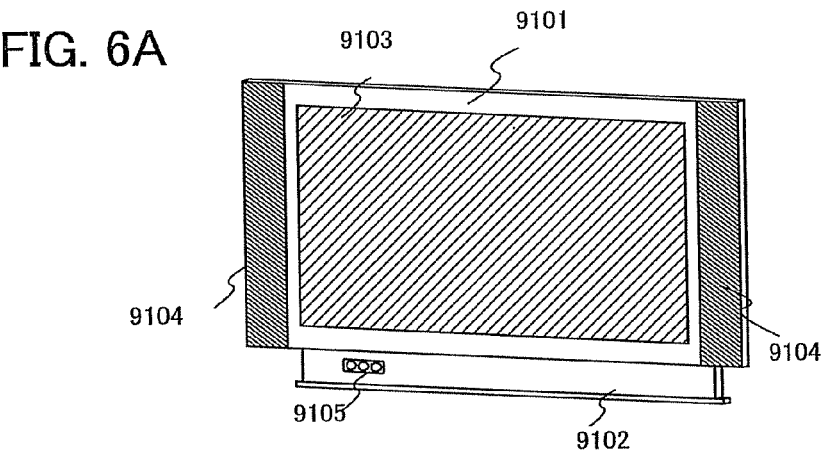
FIGS. 6A to 6D each illustrate an electronic device according to one embodiment of the present invention.

FIG. 6A illustrates a television set according to Embodiment 7. The television set includes a housing 9101, a supporting base 9102, a display portion 9103, a speaker portion 9104, a video input terminal 9105, and the like. In the television set, the display portion 9103 has light-emitting elements similar to those described in Embodiments 2 to 5, and the light-emitting elements are arranged in matrix. The light-emitting elements have features of high emission efficiency and low power consumption. In addition, the light-emitting elements have capability of red-color light emission with high luminous efficiency. Since the display portion 9103 including such light-emitting elements has similar features, this television set is free from deterioration of image quality and has low power consumption. With such features, deterioration compensating function circuits and power supply circuits can be significantly reduced or downsized in the television set, which leads to reduction in size and weight of the housing 9101 and the supporting base 9102. The television set according to Embodiment 7, which achieves low power consumption, high image quality, and reduction in size and weight can be provided as a product that is suitable for any residential environment. Further, since the light-emitting element capable of emitting red-color light with high luminous efficiency is included, a television set having a display portion with low power consumption and excellent color reproducibility can be obtained.

Figure 6B:
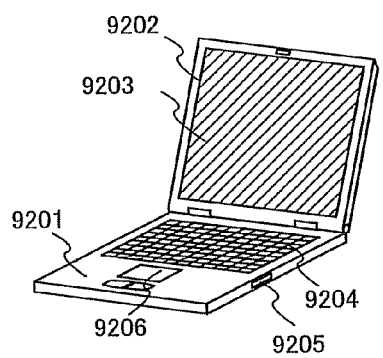

FIG. 6B illustrates a computer according to Embodiment 7. The computer includes a main body 9201, a housing 9202, a display portion 9203, a keyboard 9204, an external connection port 9205, a pointing device 9206, and the like. In the computer, the display portion 9203 has light-emitting elements similar to those described in Embodiments 2 to 5, and the light-emitting elements are arranged in matrix. The light-emitting elements have features of high emission efficiency and low power consumption. In addition, the light-emitting elements have capability of red-color light emission with high luminous efficiency. Since the display portion 9203 including such light-emitting elements has similar features, this computer is free from deterioration of image quality and has low power consumption. With such features, deterioration compensating function circuits and power supply circuits can be significantly reduced or downsized in the computer, which leads to reduction in size and weight of the main body 9201 and the housing 9202. The computer according to Embodiment 7, which achieves low power consumption, high image quality, and reduction in the size and weight, can be provided as a product that is suitable for the environment. Further, since the light-emitting element capable of emitting red-color light with high luminous efficiency is included, a computer having a display portion with low power consumption and excellent color reproducibility can be obtained.

Figure 6C:
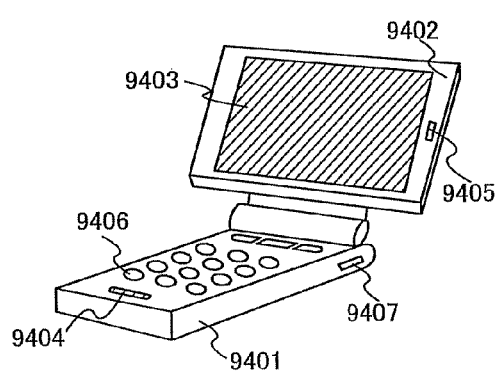

FIG. 6C illustrates a cellular phone according to Embodiment 7. The cellular phone includes a main body 9401, a housing 9402, a display portion 9403, an audio input portion 9404, an audio output portion 9405, operation keys 9406, an external connection port 9407, and the like. In the cellular phone, the display portion 9403 has light-emitting elements similar to those described in Embodiments 2 to 5, and the light-emitting elements are arranged in matrix. The light-emitting elements have features of high emission efficiency and low power consumption. In addition, the light-emitting elements have capability of red-color light emission with high luminous efficiency. Since the display portion 9403 including such light-emitting elements has similar features, this cellular phone is free from deterioration of image quality and has low power consumption. With such features, deterioration compensating function circuits and power supply circuits can be significantly reduced or downsized in the cellular phone, which leads to reduction in size and weight of the main body 9401 and the housing 9402. The cellular phone according to Embodiment 7, which achieves low power consumption, high image quality, and reduction in the size and weight, can be provided as a product that is suitable for being carried. Further, since the light-emitting element capable of emitting red-color light with high luminous efficiency is included, a cellular phone having a display portion with low power consumption and excellent color reproducibility can be obtained.

Figure 6D:
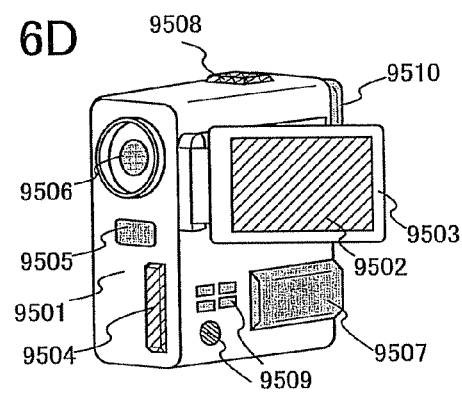

FIG. 6D illustrates a camera according to Embodiment 7. The camera includes a main body 9501, a display portion 9502, a housing 9503, an external connection port 9504, a remote control receiving portion 9505, an image receiving portion 9506, a battery 9507, an audio input portion 9508, operation keys 9509, an eyepiece portion 9510, and the like. In the camera, the display portion 9502 has light-emitting elements similar to those described in Embodiments 2 to 5, and the light-emitting elements are arranged in matrix. The light-emitting elements have features of high emission efficiency and low power consumption. In addition, the light-emitting elements have capability of red-color light emission with high luminous efficiency. Since the display portion 9502 including such light-emitting elements has similar features, this camera is free from deterioration of image quality and has low power consumption. With such features, deterioration compensating function circuits and power supply circuits can be significantly reduced or downsized in the camera, which leads to reduction in size and weight of the main body 9501. The camera according to Embodiment 7, which achieves low power consumption, high image quality, and reduction in the size and weight, can be provided as a product that is suitable for being carried. Further, since the light-emitting element capable of emitting red-color light with high luminous efficiency is included, a camera having a display portion with low power consumption and excellent color reproducibility can be obtained.

As described above, the applicable range of any of the light-emitting devices described in the above embodiment is so wide that the light-emitting device can be applied to electronic devices in various fields. By using any of the organometallic complexes described in Embodiment 1, electronic devices that each have a display portion with low power consumption and excellent color reproducibility can be provided.

Any of the light-emitting devices described in the above embodiment can also be used as a lighting device. One embodiment using the light-emitting element described in the above embodiment as a lighting device will be described with reference to FIG. 7.

Figure 7:
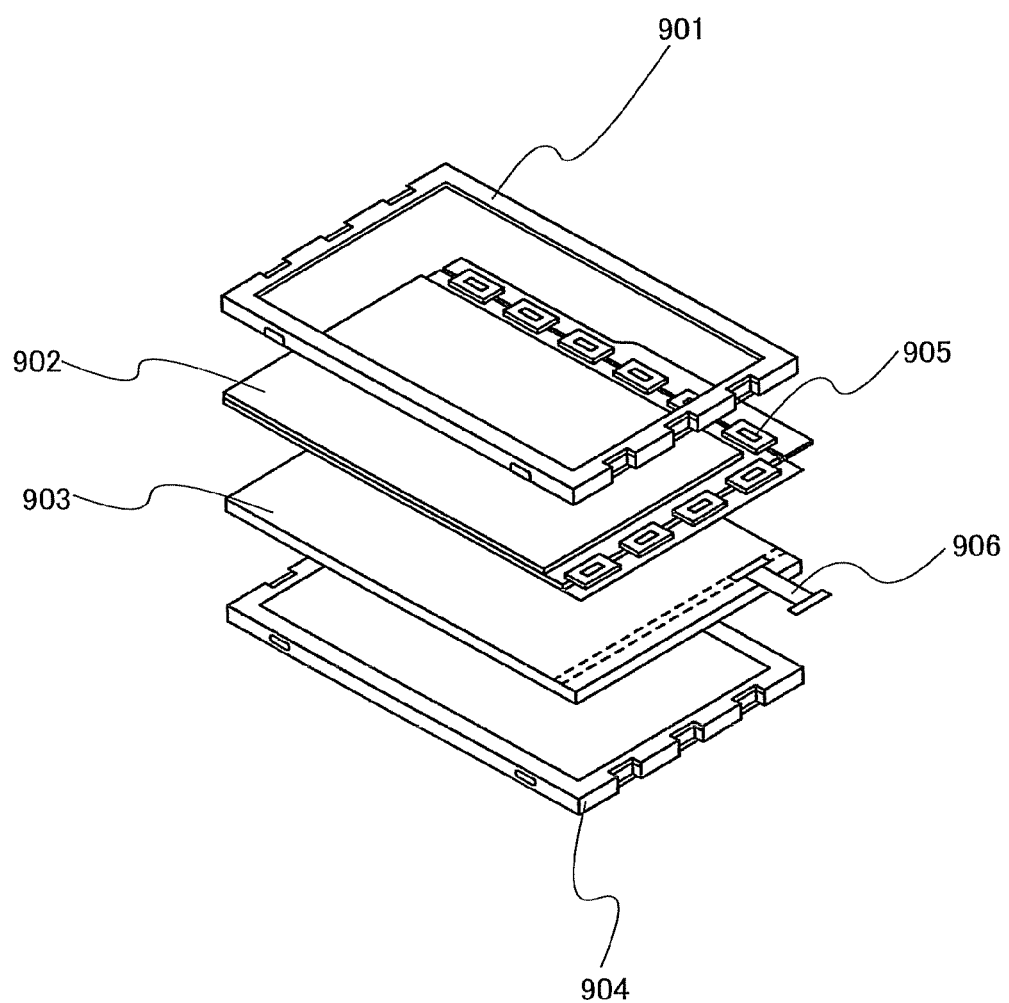
FIG. 7 illustrates an electronic device according to one embodiment of the present invention.

FIG. 7 illustrates an example of a liquid crystal display device using any of the light-emitting devices described in the above embodiment as a backlight. The liquid crystal display device illustrated in FIG. 7 includes a housing 901, a liquid crystal layer 902, a backlight 903, and a housing 904, and the liquid crystal layer 902 is connected to a driver IC 905. Any of the light-emitting devices described in the above embodiment is used as the backlight 903, and current is supplied through a terminal 906.

By using any of the light-emitting devices described in the above embodiment as a backlight of a liquid crystal display device, a backlight with low power consumption can be obtained. Any of the light-emitting devices described in the above embodiment is a lighting device with plane light emission, and can have a large area. Therefore, the backlight can have a large area, and thus a liquid crystal display device having a large area can be realized. Furthermore, any of the light-emitting devices described in the above embodiment has a thin shape and consumes low power, and thus a thin shape and low power consumption of a display device can also be realized.

Figure 8:
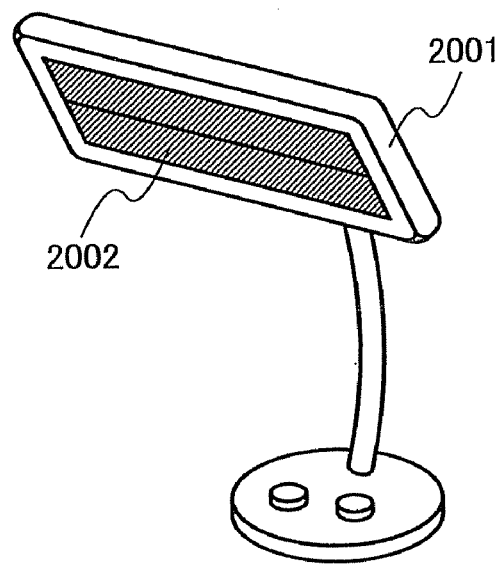
FIG. 8 illustrates a lighting device according to one embodiment of the present invention.

FIG. 8 illustrates an example of using the light-emitting device to which any of the organometallic complexes described in Embodiment 1 is applied as a table lamp that is a lighting device. The table lamp illustrated in FIG. 8 includes a housing 2001 and a light source 2002 to which any of the light-emitting devices described in the above embodiment is applied. Accordingly, a light-emitting device with low power consumption can be realized.

Figure 9:
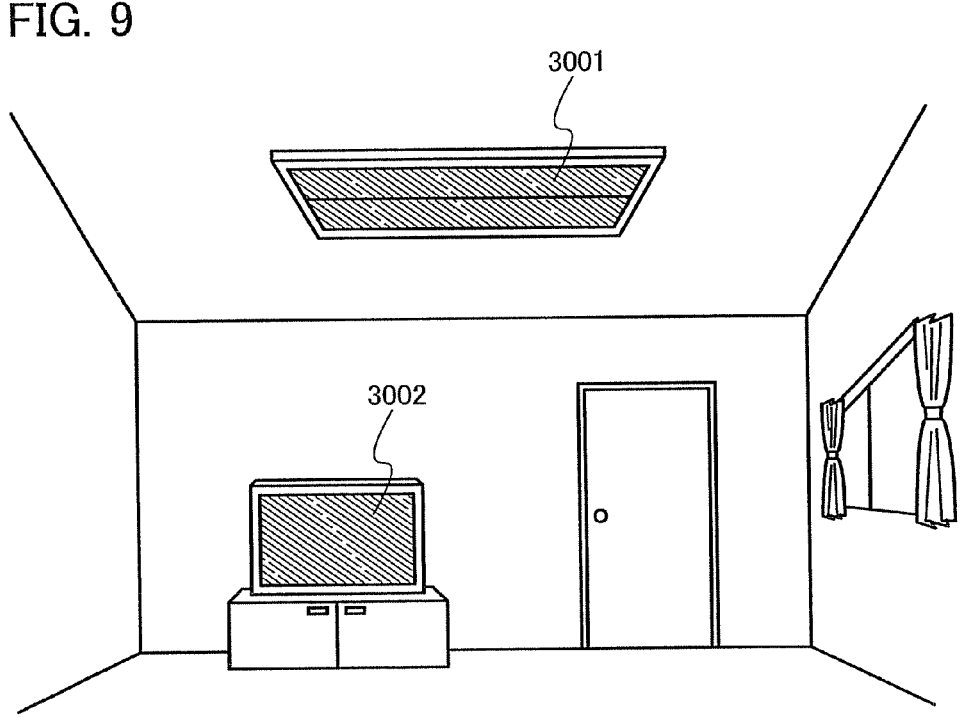
FIG. 9 illustrates a lighting device according to one embodiment of the present invention.

FIG. 9 illustrates an example of using the light-emitting device to which any of the organometallic complexes described in Embodiment 1 is applied as an indoor lighting device 3001. This light-emitting device can have a large area, so that it can be used as a lighting device with a large area. Further, this light-emitting device has a thin shape and consumes low power, and thus can be used as a lighting device with a thin shape and low power consumption. In a room where the light-emitting device described in Embodiment 7 is used as the indoor lighting device 3001, a television set 3002, as illustrated in FIG. 6A, can be placed.

Example 1

Synthesis Example 1

Synthesis Example 1 will specifically exemplify a synthesis example of (acetylacetonato)bis[5-(3-cyanophenyl)-2,3-diphenylpyrazinato]iridium(III) (abbreviation: [Ir(dppr-3CP)$_2$(acac)] which is an organometallic complex of one embodiment of the present invention, represented by the structural formula (1) in Embodiment 1.

Step 1: Synthesis of
5-(3-cyanophenyl)-2,3-diphenylpyrazine
(abbreviation: Hdppr-3 CP)

First, 1.02 g of 2,3-diphenyl-5-chloropyrazine, 0.62 g of 3-cyanophenylboronic acid, 0.15 g of tetrakis triphenylphosphine palladium(0) (abbreviation: Pd(PPh$_3$)$_4$), 10 mL of toluene, 1.5 mL of ethanol, 1.16 g of potassium carbonate, 4.2 mL of water were put in an eggplant-type flask with a reflux pipe, and the atmosphere in the flask was substituted with argon. Then, irradiation with microwave (2.45 GHz, 100 W to 150 W) was performed for 45 minutes to cause a reaction. Water was added to this mixture and dichloromethane was used as an extraction solvent, so that an organic layer was extracted. The obtained organic layer was dried with anhydrous magnesium sulfate. After the drying, the solution was filtrated. After a solvent of this solution was distilled off, the residue obtained by the distillation was purified by silica gel column chromatography which uses a mixture solution of dichloromethane and ethyl acetate as a developing solvent to obtain a white powdered solid in a yield of 42%. Note that the irradiation with a microwave was performed using a microwave synthesis system (Discover, produced by CEM Corporation). A synthesis scheme of Step 1 is shown by the following (a-1).

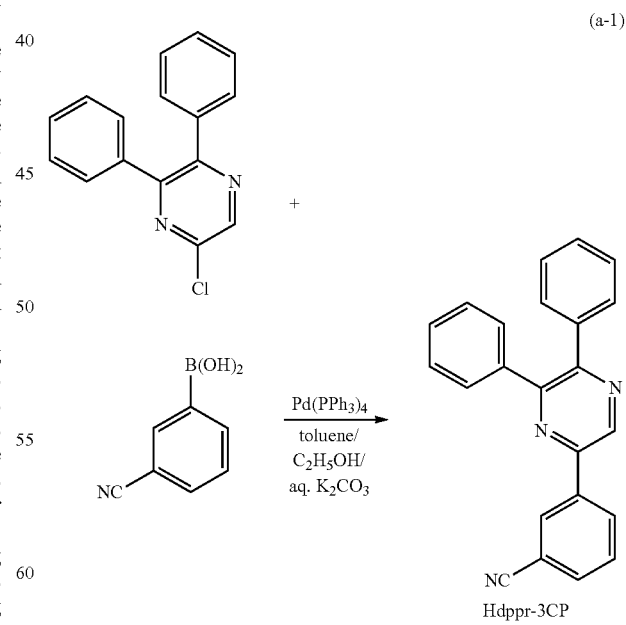

(a-1)

By a nuclear magnetic resonance (NMR) method, this compound was confirmed to be 5-(3-cyanophenyl)-2,3-diphenylpyrazine (abbreviation: Hdppr-3CP) which was the desired compound.

$^1$H NMR data of the obtained compound is shown below.
$^1$H-NMR. δ(CDCl$_3$): 7.30-7.41 (m, 6H), 7.50-7.58 (m, 4H), 7.64 (t, 1H), 7.76 (d, 1H), 8.37 (d, 1H), 8.51 (s, 1H), 9.04 (s, 1H).

Figure 10:
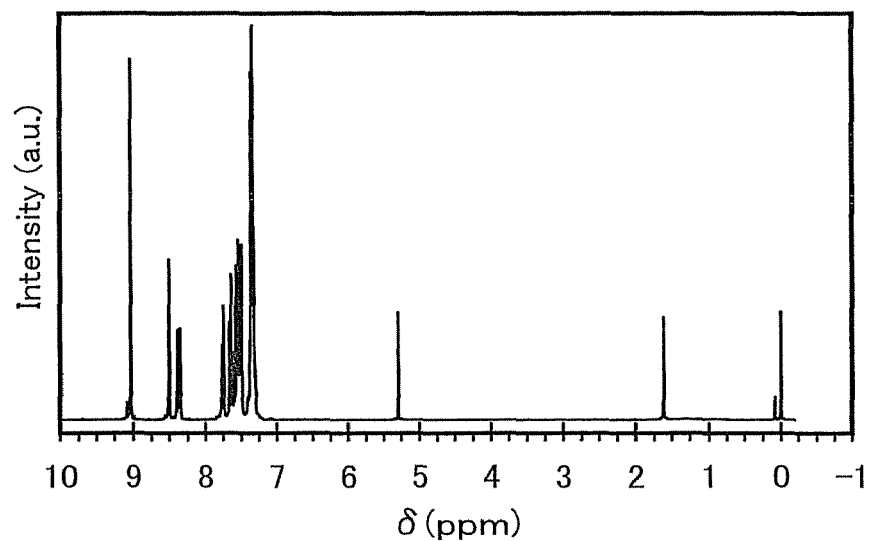
FIG. 10 is a $^1$H-NMR chart of 5-(3-cyanophenyl)-2,3-diphenylpyrazine.

Further, a $^1$H NMR chart is illustrated in FIG. 10.

Step 2: Synthesis di-μ-chloro-bis[bis{5-(3-cyanophenyl)-2,3-diphenylpyrazinato}iridium(III)] (abbreviation: [Ir(dppr-3CP)$_2$Cl]$_2$)

Subsequently to Step 1, 6 mL of 2-ethoxyethanol, 2 mL of water, 0.52 g of the pyrazine derivative Hdppr-3CP obtained in the above Step 1, and 0.22 g of iridium chloride hydrate (IrCl$_3$·H$_2$O) (produced by Sigma-Aldrich Corp.) were put in an eggplant-type flask with a reflux pipe, and the atmosphere in the flask was substituted with argon. Then, irradiation with microwave (2.45 GHz, 100 W) was performed for 30 minutes to cause a reaction. The orange powder precipitated from the reaction solution was filtered, and the residue was washed with ethanol to obtain a dinuclear complex [Ir(dppr-3CP)$_2$Cl]$_2$ (yield: 70%). A synthesis scheme of Step 2 is shown by the following (b-1).

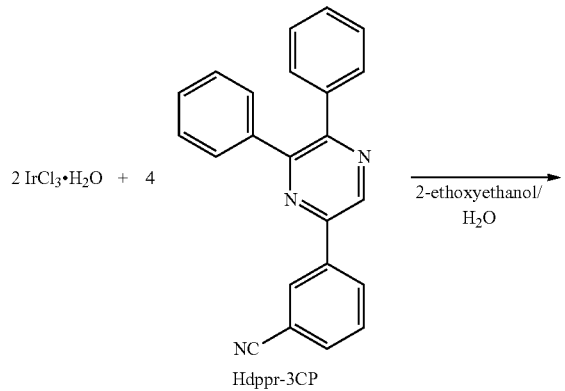

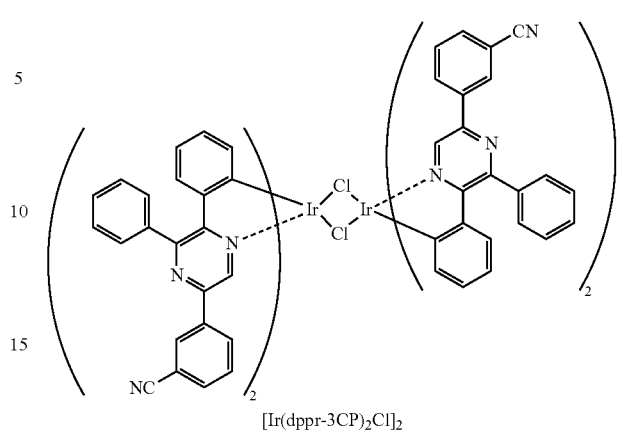

(b-1)

Step 3: Synthesis of (acetylacetonato)bis[5-(3-cyanophenyl)-2,3-diphenylpyrazinato]iridium(III) (abbreviation: [Ir(dppr-3CP)$_2$(acac)]

Subsequently to Step 2, 10 mL of 2-ethoxyethanol, 0.46 g of the dinuclear complex [Ir(dppr-3CP)$_2$Cl]$_2$ obtained in the above Step 2, 0.081 mL of acetylacetone, and 0.28 g of sodium carbonate were put in an eggplant-type flask with a reflux pipe, and the atmosphere in the flask was substituted with argon. Then, irradiation with microwave (2.45 GHz, 100 W) was performed for 20 minutes to cause a reaction. The reaction solution was filtered, and then a solvent of the obtained filtrate was distilled off. The residue obtained by distillation was recrystallized with methanol to obtain a red-color powdered solid in a yield of 6%. A synthesis scheme of Step 3 is shown by the following (c-1).

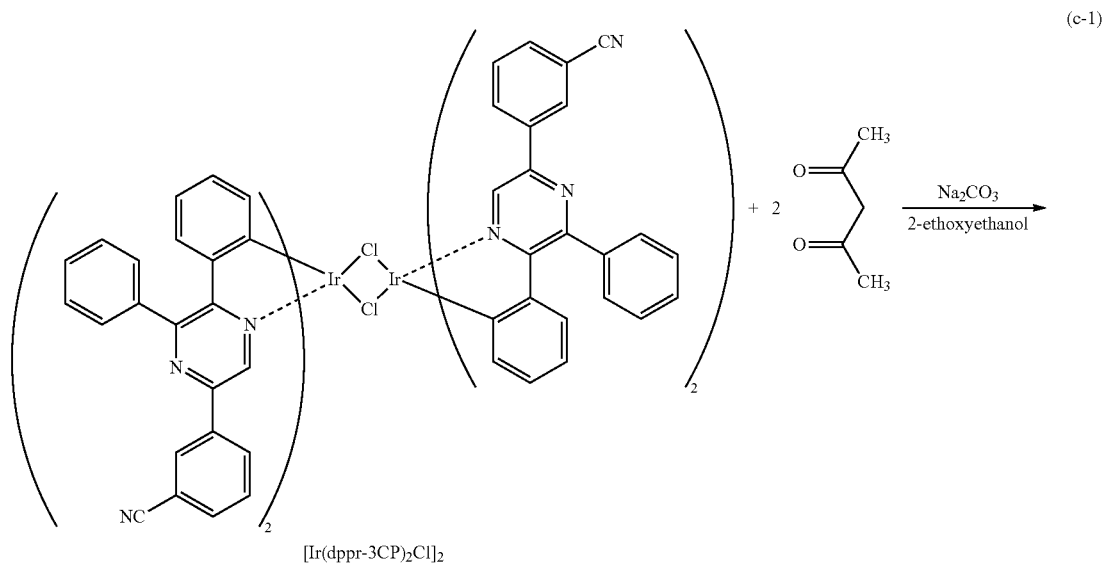

(c-1)

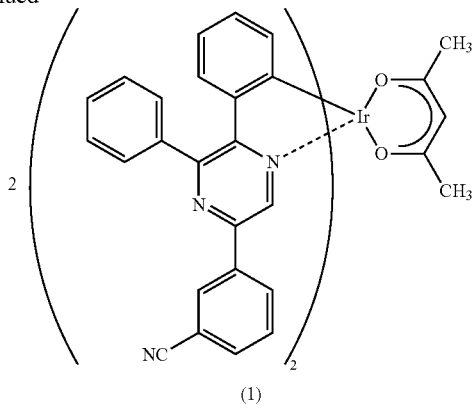

(1)

By a nuclear magnetic resonance (NMR) method, this compound was confirmed to be di-μ-chloro-bis[bis{5-(3-cyanophenyl)-2,3-diphenylpyrazinato}iridium(III)] (abbreviation: [Ir(dppr-3CP)$_2$Cl]$_2$) which was the desired compound.

$^1$H NMR data of the obtained compound is shown below.
$^1$H-NMR. δ(CDCl$_3$): 1.95 (s, 6H), 5.39 (s, 1H), 6.44 (d, 2H), 6.54 (t, 2H), 6.70 (t, 2H), 6.96 (d, 2H), 7.57-7.66 (m, 8H), 7.73-7.83 (m, 6H), 8.25 (d, 2H), 8.42 (s, 2H), 8.95 (s, 2H).

Figure 11:
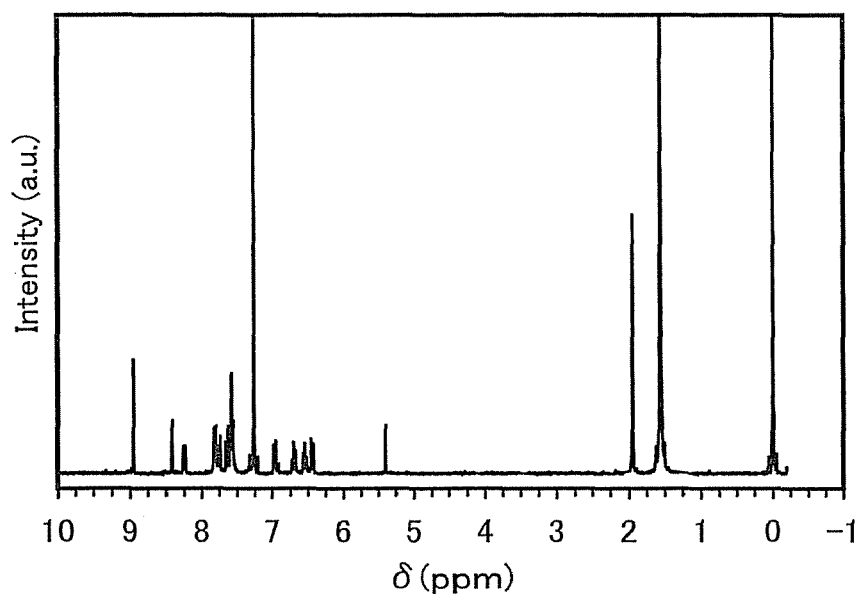
FIG. 11 is a $^1$H-NMR chart of (acetylacetonato)bis[5-(3-cyanophenyl)-2,3-diphenylpyrazinato]iridium(III)

Further, a $^1$H NMR chart is illustrated in FIG. 11.

Figure 12:
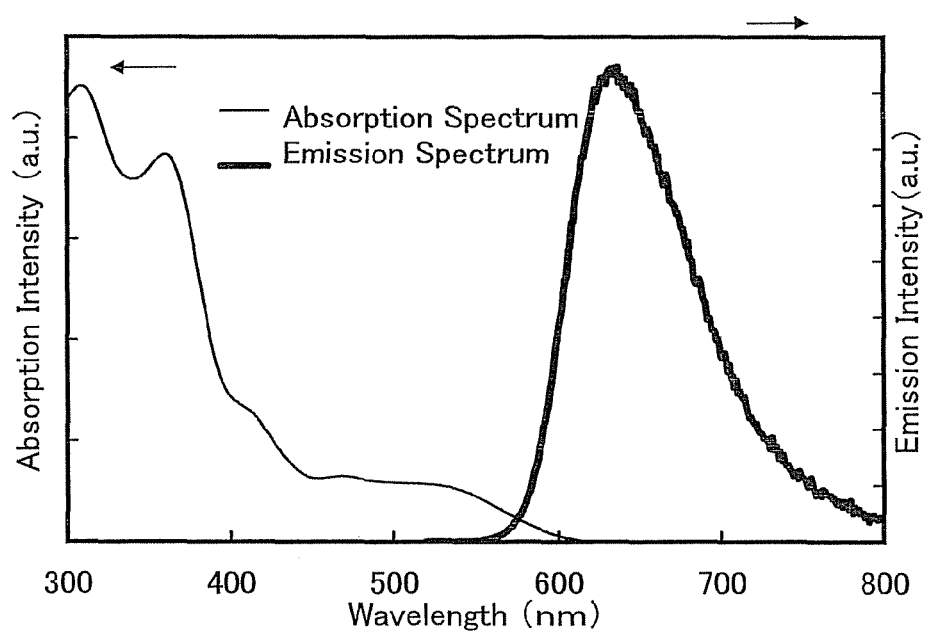
FIG. 12 is a graph showing an absorption spectrum and an emission spectrum of (acetylacetonato)bis[5-(3-cyanophenyl)-2,3-diphenylpyrazinato]iridium(III).

Next, an absorption spectrum of [Ir(dppr-3CP)$_2$(acac)] was measured. With use of an ultraviolet-visible light spectrophotometer (produced by Japan Spectroscopy Corporation, V550 type), the absorption spectrum was measured using a chloroform solution at room temperature. Further, an emission spectrum of [Ir(dppr-3CP)$_2$(acac)] was measured. With use of a fluorescence spectrophotometer (produced by Hamamatsu Photonics Corporation, FS920), the emission spectrum was measured using a degassed chloroform solution at room temperature. A measurement result is illustrated in FIG. 12. In FIG. 12, the horizontal axis represents wavelength and the vertical axis represents absorption intensity and emission intensity.

As illustrated in FIG. 11, the organometallic complex of one embodiment of the present invention represented by the structural formula (1), [Ir(dppr-3CP)$_2$(acac)], has a peak of emission spectrum at 632 nm, and red-color light emission from the chloroform solution was observed.

This application is based on Japanese Patent Application serial no. 2008-273194 filed with Japan Patent Office on Oct. 23, 2008, the entire contents of which are hereby incorporated by reference.

What is claimed is:

1. A light-emitting element comprising an organometallic complex represented by a formula (G2),

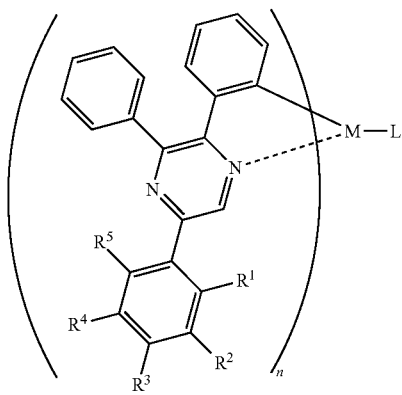

(G2)

wherein R$^1$, R$^2$, R$^3$, R$^4$ and R$^5$ each represent hydrogen or a cyano group, and at least one of R$^1$, R$^2$, R$^3$, R$^4$ and R$^5$ is a cyano group;

wherein L represents a monoanionic ligand selected from the group consisting of a monoanionic bidentate chelate ligand having a β-diketone structure, a monoanionic bidentate chelate ligand having a carboxy group, a monoanionic bidentate chelate ligand having a phenolic hydroxy group, and a monoanionic bidentate chelate ligand in which two ligand elements are both nitrogen;

wherein M represents iridium; and wherein n is 2.

2. The organometallic complex according to claim 1, wherein the monoanionic ligand is a monoanionic ligand represented by any of structural formulae (L1), (L2), (L3), (L4), (L5), (L6), (L7) and (L8)

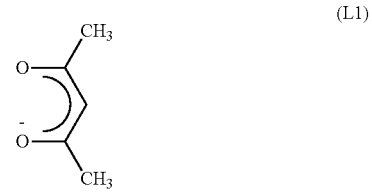

(L1)

-continued (L2) 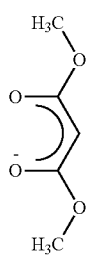

(L3) 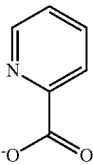

(L4) 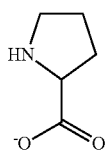

(L5) 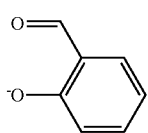

(L6) 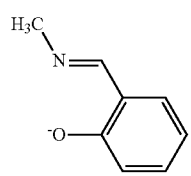

(L7) 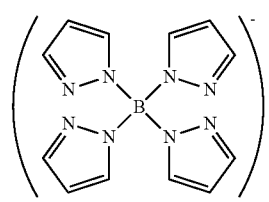

(L8) 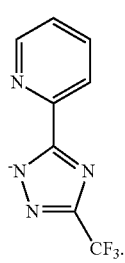

3. A light-emitting element comprising an organometallic complex represented by a formula (G2),

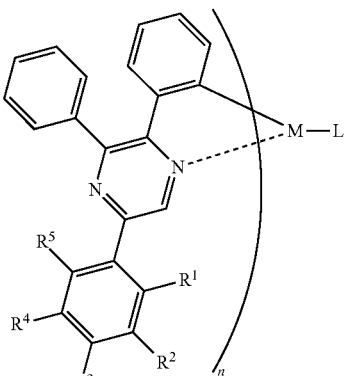
(G2)

wherein $R^1$, $R^2$, $R^3$, $R^4$ and $R^5$ each represent hydrogen or a cyano group, and any one of $R^1$, $R^2$, $R^3$, $R^4$ and $R^5$ is a cyano group;

wherein L represents a monoanionic ligand selected from the group consisting of a monoanionic bidentate chelate ligand having a β-diketone structure, a monoanionic bidentate chelate ligand having a carboxy group, a monoanionic bidentate chelate ligand having a phenolic hydroxy group, and a monoanionic bidentate chelate ligand in which two ligand elements are both nitrogen;

wherein M represents iridium; and wherein n is 2.

4. The organometallic complex according to claim 3, wherein the monoanionic ligand is a monoanionic ligand represented by any of structural formulae (L1), (L2), (L3), (L4), (L5), (L6), (L7) and (L8)

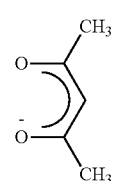
(L1)

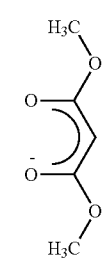
(L2)

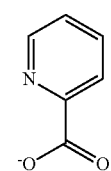
(L3)

-continued
(L4)
(L5)
(L6)
(L7)
(L8)
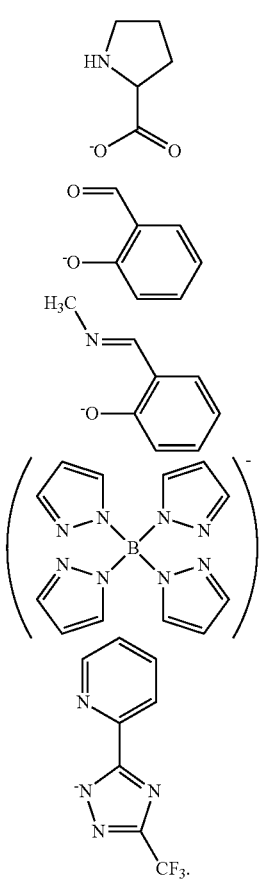
5. A light-emitting element comprising an organometallic complex represented by a formula (1)
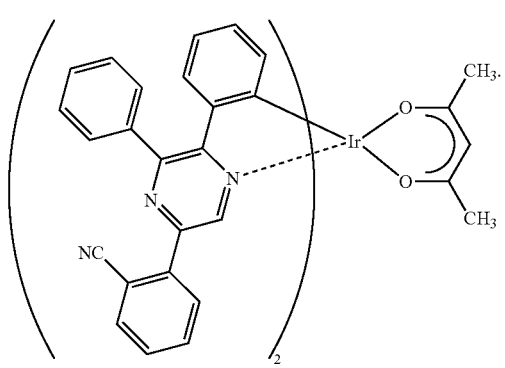
(1)
6. A light-emitting element comprising an organometallic complex represented by a formula (2)
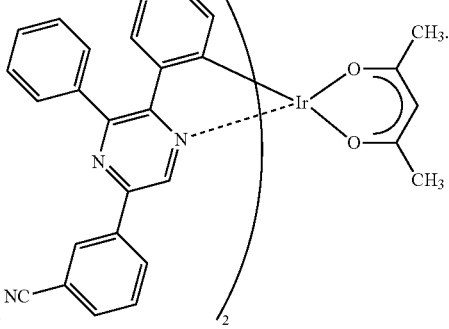
(2)
7. A light-emitting element comprising an organometallic complex represented by a formula (3)
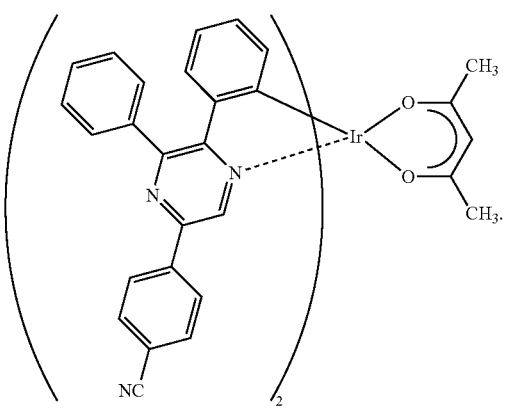
(3)
* * * * *